United States Patent
Sturgis et al.

(10) Patent No.: US 11,458,049 B2
(45) Date of Patent: Oct. 4, 2022

(54) ABSORBENT ARTICLES INCLUDING PERFUME AND CYCLODEXTRINS

(71) Applicant: The Procter & Gamble Company, Cincinnati, OH (US)

(72) Inventors: David Arthur Sturgis, Montgomery, OH (US); Jianjun Justin Li, West Chester, OH (US); Marc Adam Flickinger, West Chester, OH (US); Virginia Tzung Hwei Hutchins, Cincinnati, OH (US); Steven Louis Diersing, Cincinnati, OH (US); Steven Michael Wujek, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1278 days.

(21) Appl. No.: 15/696,214

(22) Filed: Sep. 6, 2017

(65) Prior Publication Data
US 2018/0064588 A1    Mar. 8, 2018

Related U.S. Application Data

(60) Provisional application No. 62/383,727, filed on Sep. 6, 2016.

(51) Int. Cl.
*A61F 13/84* (2006.01)
*A61L 15/28* (2006.01)
*A61L 15/46* (2006.01)

(52) U.S. Cl.
CPC .......... *A61F 13/8405* (2013.01); *A61L 15/28* (2013.01); *A61L 15/46* (2013.01); *A61F 2013/8408* (2013.01); *A61L 2300/62* (2013.01); *A61L 2300/802* (2013.01)

(58) Field of Classification Search
CPC ...... A61L 15/28; A61L 15/46; A61L 2300/62; A61L 2300/802; A61F 13/8405; A61F 2013/8408
USPC ......................................................... 604/259
See application file for complete search history.

(56) References Cited

U.S. PATENT DOCUMENTS

| | | |
|---|---|---|
| 4,049,792 A | 9/1977 | Elsnau |
| 4,731,243 A | 3/1988 | Lindauer et al. |
| 4,803,195 A | 2/1989 | Holzner |
| 5,094,761 A | 3/1992 | Trinh et al. |
| 5,403,828 A | 4/1995 | Lewis et al. |

(Continued)

FOREIGN PATENT DOCUMENTS

| | | |
|---|---|---|
| EP | 0392608 | 10/1990 |
| EP | 1024785 | 1/2003 |

(Continued)

OTHER PUBLICATIONS

U.S. Appl. No. 15/696,268, filed Sep. 6, 2017, Sturgis et al.

(Continued)

*Primary Examiner* — Andrew J Mensh
(74) *Attorney, Agent, or Firm* — Gary J. Foose

(57) ABSTRACT

An absorbent article comprising a perfume which is suitable for improved release from a cyclodextrin complex, wherein the perfume includes 10% or more, by weight of the perfume, of one or more perfume raw materials having: a cyclodextrin complex stability constant (log k) of less than about 3.0, a ClogP of about 2.5 or less, and a weight average molecular weight of about 200 Daltons or less.

13 Claims, 4 Drawing Sheets

(56) References Cited

U.S. PATENT DOCUMENTS

| | | | |
|---|---|---|---|
| 5,429,628 A * | 7/1995 | Trinh | A61K 8/0208 604/359 |
| 5,429,816 A | 7/1995 | Hofrichter et al. | |
| 5,718,887 A | 2/1998 | Wolf et al. | |
| 5,723,420 A | 3/1998 | Wei et al. | |
| 5,840,287 A | 11/1998 | Guskey et al. | |
| 5,840,289 A | 11/1998 | Hall | |
| 5,861,144 A | 1/1999 | Peterson et al. | |
| 5,882,638 A | 3/1999 | Dodd et al. | |
| 5,897,854 A | 4/1999 | Lucas et al. | |
| 5,968,489 A | 10/1999 | Swaile et al. | |
| 6,013,248 A | 1/2000 | Luebbe et al. | |
| 6,110,449 A | 8/2000 | Bacon et al. | |
| 6,123,932 A | 9/2000 | Guskey et al. | |
| 6,287,603 B1 | 9/2001 | Prasad et al. | |
| 6,352,688 B1 | 3/2002 | Scavone et al. | |
| 6,824,763 B2 | 11/2004 | Brooks | |
| 6,835,373 B2 | 12/2004 | Kolodzik et al. | |
| 6,893,647 B1 | 5/2005 | Malton et al. | |
| 6,936,242 B2 | 8/2005 | Elliott et al. | |
| 7,041,337 B2 | 5/2006 | Heltovics et al. | |
| 7,208,462 B2 | 4/2007 | Heltovics et al. | |
| 7,208,463 B2 | 4/2007 | Heltovics et al. | |
| 7,208,464 B2 | 4/2007 | Heltovics et al. | |
| 7,208,465 B2 | 4/2007 | Heltovics et al. | |
| 7,407,650 B2 | 8/2008 | Heltovics et al. | |
| 7,413,731 B2 | 8/2008 | Heltovics et al. | |
| 8,147,808 B2 | 4/2012 | Scavone et al. | |
| 8,632,755 B2 | 1/2014 | Scavone et al. | |
| 9,222,055 B2 | 12/2015 | Fraser et al. | |
| 9,649,386 B2 | 5/2017 | Scavone et al. | |
| 2002/0007055 A1 | 1/2002 | Uchiyama et al. | |
| 2003/0060379 A1 | 3/2003 | Souter et al. | |
| 2003/0069165 A1 | 4/2003 | Malton et al. | |
| 2003/0232730 A1 * | 12/2003 | Holland | A61K 8/738 510/101 |
| 2006/0243322 A1 | 11/2006 | Heltovics et al. | |
| 2008/0194454 A1 * | 8/2008 | Morgan | C11D 3/507 512/1 |
| 2008/0213191 A1 | 9/2008 | Scavone et al. | |
| 2008/0213203 A1 | 9/2008 | Scavone et al. | |
| 2008/0213204 A1 | 9/2008 | Scavone et al. | |
| 2008/0215023 A1 * | 9/2008 | Scavone | A61K 8/02 604/359 |
| 2009/0010972 A1 | 1/2009 | Modafari et al. | |
| 2009/0029020 A1 | 1/2009 | Strassburger | |
| 2010/0152306 A1 * | 6/2010 | Warr | A61K 8/34 514/785 |
| 2014/0180228 A1 | 6/2014 | Caputi et al. | |

FOREIGN PATENT DOCUMENTS

| | | |
|---|---|---|
| JP | 2001316219 A | 11/2001 |
| KR | 20150070937 | 6/2015 |
| WO | WO02069924 A1 | 9/2002 |
| WO | WO2014205047 | 12/2014 |

OTHER PUBLICATIONS

U.S. Appl. No. 15/696,274, filed Sep. 6, 2017, Sturgis et al.
U.S. Appl. no. 15/696,262, filed Sep. 6, 2017, Sturgis et al.
All Office Actions, U.S. Appl. No. 15/696,268.
All Office Actions, U.S. Appl. No. 15/696,274.
All Office Actions, U.S. Appl. No. 15/696,282.
All Office Actions, U.S. Appl. No. 11/712,771.
All Office Actions, U.S. Appl. No. 12/036,490.
14486 PCT International Search Report, dated Nov. 28, 2017 (166 pages).
14488 International Search Report dated Nov. 29, 2017 (166 pages).
14489 PCT International Search Report dated Oct. 30, 2017 (12 pages).
10728 International Search Report dated Sep. 1, 2009 (9 pages).
10728R International Search Report dated Apr. 6, 2009 (167 pages).
14491M PCT International Search Report, dated Nov. 29, 2017, 54 pages.

* cited by examiner

ABSORBENT ARTICLES INCLUDING PERFUME AND CYCLODEXTRINS

FIELD OF THE INVENTION

This application generally relates to absorbent articles comprising perfume and cyclodextrin complexes. The invention also relates to methods of making and using said absorbent articles.

BACKGROUND OF THE INVENTION

Perfumes are utilized to help make products more delightful to consumers. This delight can result when the perfumes mask or reduce odor as well as impart pleasant odors to products that are consumed or used by consumed by consumers.

Products like absorbent articles according to the present invention are articles which can be used to absorb any type of fluid. These articles include absorbent hygienic articles (like for example sanitary napkins, panty liners, tampons, inter labial articles, adult incontinence articles such as adult incontinence pads, pants and diapers, baby pants and diapers, pessaries, breast pads and hemorrhoid pads). Other absorbent articles according to the present invention can be for example absorbent paper towels, wipes, toilet paper, or facial tissues as well as absorbent articles used in the medical field, such as wound dressings and surgical articles, and absorbent articles used in food technology and conservation (such as fluid pads for meat, fish and so on). Absorbent articles according to the present invention include absorbent materials used industrially to absorb fluids, for example, those used to contain spillage of chemicals.

Absorbent articles are commonly used to absorb and retain bodily fluids and other exudates excreted by the human or animal body, such as urine, menses, blood, fecal materials or mucus or chemicals or any type of fluid waste. Paper towels, wipes, facial tissues and toilet paper may be used also to absorb kitchen and food residues and/or any kind of dirt or waste. In many cases the absorbed materials, can be malodorous or capable of generating malodors over time while the article is still being used or after it has been disposed.

As one would imagine, once such absorbent articles have been acted on by a consumer, i.e., a fluid has contacted it, the articles tend to give off a malodor. As a result, materials for controlling and reducing malodors in absorbent articles have been identified in the art. Among them conventional perfumes have been commonly used. Conventional perfumes, however, are typically not completely satisfactory in absorbent articles where it is necessary that the perfume express and maintains a defined perfume character for a long time. Absorbent hygienic articles are worn for many hours and also absorbent articles after disposal may still have an unpleasant odor so that a perfume should desirably continue to be perceived even after disposal of the article. Cyclodextrins have been to be employed in such absorbent articles to assist in the management of malodor. Currently, however, perfumes are not optimized for release from a cyclodextrin complex and some components can remain within the complex and unexpressed. As such, there is a need for absorbent articles that include a perfume which is optimized for release from a cyclodextrin and cyclodextrin complexes made from such optimized perfumes.

SUMMARY OF THE INVENTION

An absorbent article comprising a perfume which comprises perfume raw materials, wherein 10% or more, by weight of the perfume, of the perfume raw materials have: a cyclodextrin complex stability constant (log k) of less than about 3.0, a ClogP of about 2.5 or less, and a weight average molecular weight of about 200 Daltons or less.

An absorbent article comprising a cyclodextrin complex which further comprises a cyclodextrin and a perfume, wherein the wherein 10% or more, by weight of the perfume, of the perfume raw materials have: a cyclodextrin complex stability constant is about 3.0 or less, a ClogP of about 2.5 or less, and a weight average molecular weight of about 200 Daltons or less.

These and other combinations are possible and are described in more detail below.

DETAILED DESCRIPTION OF THE INVENTION

Figure 1:
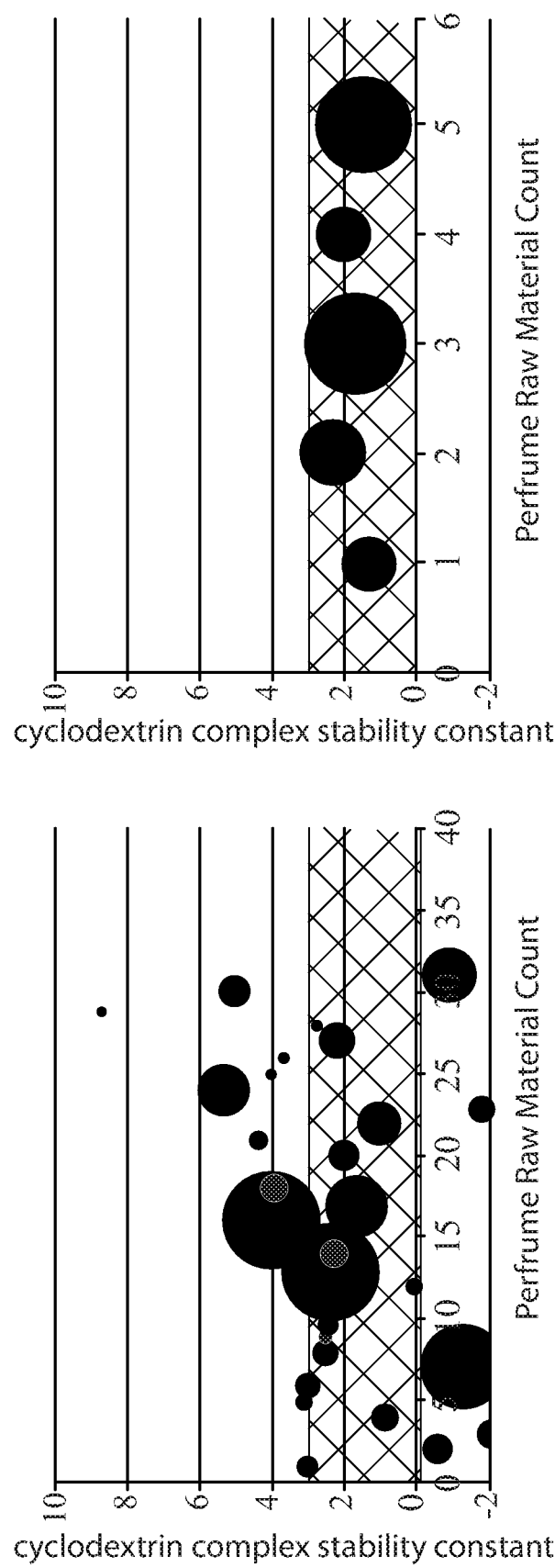
FIG. 1 is a side-by-side comparison of the cyclodextrin complex stability constant (BCD binding strength) of a perfume before and after optimization for release from a cyclodextrin complex.

"Absorbent article" refers to articles that absorb any type of fluid. These articles are typically disposable and include paper towels, wipes, toilet paper, facial tissue, absorbent articles used in the medical field such as wound dressings and surgical articles, absorbent articles used in food technology and conservation (such as fluid pads for meat, fish and the like), absorbent articles used industrially to absorb fluids, and absorbent hygienic articles. The term "absorbent hygienic articles" refers to devices that absorb and contain body exudates, such as urine, menses, blood and feces. The term "disposable" is used herein to describe absorbent articles which are not intended to be laundered or otherwise restored or reused as an absorbent article after a single use. Examples of absorbent hygienic articles include diapers, toddler training pants, adult incontinence pants, pads or diapers, and feminine hygiene garments such as sanitary napkins, pantiliners, tampons, interlabial articles, breast pads, hemorrhoid pads, and the like.

Absorbent hygienic articles and components thereof, including the topsheet, backsheet, absorbent core, and any individual layers of these components, can have a body-facing surface and a garment-facing surface. As used herein, "body-facing surface" means that surface of the article or component which is intended to be worn toward or adjacent to the body of the wearer, while the "garment-facing surface" is on the opposite side and is intended to be worn toward or placed adjacent to the wearer's undergarments when the disposable absorbent article is worn.

As used herein, the term "perfume" includes a fine fragrance composition intended for application to a body or product surface, such as for example, skin or hair, i.e., to impart a pleasant odor thereto, or cover a malodour thereof. The fine fragrance compositions may be ethanol based compositions.

As used herein, the term "consumer" means both the user of the absorbent article and the observer nearby or around the user.

As used herein, the term "cyclodextrin" includes any of the known cyclodextrins such as unsubstituted cyclodextrins containing from about six to about twelve glucose units, especially alpha-cyclodextrin, beta-cyclodextrin, gamma-cyclodextrin and/or their derivatives and/or mixtures thereof. For example, cyclodextrins may be selected from the group consisting of beta-cyclodextrin, hydroxypropyl alpha-cyclodextrin, hydroxypropyl beta-cyclodextrin, methylated-alpha-cyclodextrin, methylated-beta-cyclodextrin, and mixtures thereof.

"Cyclodextrin complex stability constant" (log K) refers to the ability of a perfume raw material to bind to a cyclodextrin. The complex stability constant of a multitude of materials with respect to various cyclodextrins as measured by the calorimetry technique can be found in the literature, for example, Rekharsky and Inoue (1998), Complexation Thermodynamics of Cyclodextrins, Chemical Review, 98, 1875-1917. In addition, for reference, a list of perfume raw materials and their estimated complex stability constants is included in a table below.

"ClogP" refers to calculated log P values, which is a measure of a compound's hydrophilicity, wherein log P is the octanol water partitioning coefficient as computed by the Consensus algorithm implemented in ACD/Percepta version 14.02 by Advanced Chemistry Development, Inc. (ACD/Labs, Toronto, Canada).

"Odor Detection Threshold" refers to the lowest concentration of a certain odor compound that is perceivable to the human sense of smell. The Odor Detection Threshold of a multitude of materials can be found in van Gernert, L. J.; *Odour Thresholds* (*Compilations of Odour Threshold Values in Air, Water and Other Media*; Oliemans Punter & Partners; The Netherlands, 2011. It is in units of −log molar concentration. In this context, human odor detection thresholds (ODTs) are expressed as olfactory power, or p.ol (the negative log of the molar concentration of the odorant in the air at which a human first detects the presence of the odorant). These values can be directly transposed to other commonly used units such as ppm (volume) and ppb (volume): thresholds of 1 ppm and 1 ppb are equivalent to p.ol=6 and p.ol=9, respectively. Odor Detection Threshold can be measured, for instance, by the method in International Publication WO 2006/138726.

"Cyclodextrin complex" or even "cyclodextrin complex" refers to a complex of cyclodextrin and perfume.

"Molecular weight," unless otherwise designated, refers to the weight average molecular weight which can be calculated by using the sum of the molecular weights of the elements in a molecule. These can be found, for example, in *Atomic Weights of the Elements*, Weiser, 2005.

"Room temperature as used herein refers to about 20° C.

Many consumers enjoy a pleasant scent in absorbent article consumer products, especially during use. Scent can be delivered through a multitude of means, like direct addition of a scent to a product or through the use of a scent delivery agent. Scent delivery agents can enhance and/or change the delivery of the scent. For example, some delivery agents can encapsulate a perfume so that it can be released upon a triggering event. Other delivery agents can help a perfume deposit onto a target surface so that the perfume is more easily detected by the consumer.

The perfumes that provide these pleasant scents are usually not a single component, but are made up of multiple perfume raw materials which when combined give the overall scent of the perfume. Each of the perfume raw materials has its own characteristic and its own chemical properties, like molecular weight, cLogP, etc. These properties can influence where and how long a scent can be detected. Some of these properties are how perfume raw materials are divided into top, middle, and base notes.

Cyclodextrin Complex

A cyclodextrin is a complexing material that may be used for substantially "hiding" one or more perfume raw materials until a triggering mechanism has occurred, such as, for example, perspiration, urination, or menstruation, to "release" the perfume raw material. Therefore, these are well suited for use in absorbent articles where masking and/or odor control is desirable after the triggering mechanism. As used herein, the term "cyclodextrin" includes any of the known cyclodextrins such as unsubstituted cyclodextrins containing from about six to about twelve glucose units, especially alpha-cyclodextrin, beta-cyclodextrin, gamma-cyclodextrin and/or their derivatives and/or mixtures thereof. For example, cyclodextrins may be selected from the group consisting of beta-cyclodextrin, hydroxypropyl alpha-cyclodextrin, hydroxypropyl beta-cyclodextrin, methylated-alpha-cyclodextrin, methylated-beta-cyclodextrin, and mixtures thereof. Cyclodextrins may be included within a cyclodextrin complex in an amount of from at least about 0.1%, from at least about 1%, from at least about 2%, or from at least about 3%; to about 25%, to about 20%, to about 15% or to about 10%, by weight of the cyclodextrin complex.

Previously, when using a perfume in combination with a delivery agent, like a cyclodextrin, it was believed that most of the perfume was released from the delivery agent upon the triggering event. For cyclodextrins, the triggering event is usually the introduction of moisture. However, it was recently discovered that only about 4%, of a complexed perfume, was being released from a cyclodextrin upon exposure to moisture. As such, most of the perfume was remaining within the cyclodextrin and was not noticeable to the consumer as desired. This means there is significant room for improvement in the efficacy of cyclodextrin complexes.

Figure 3:
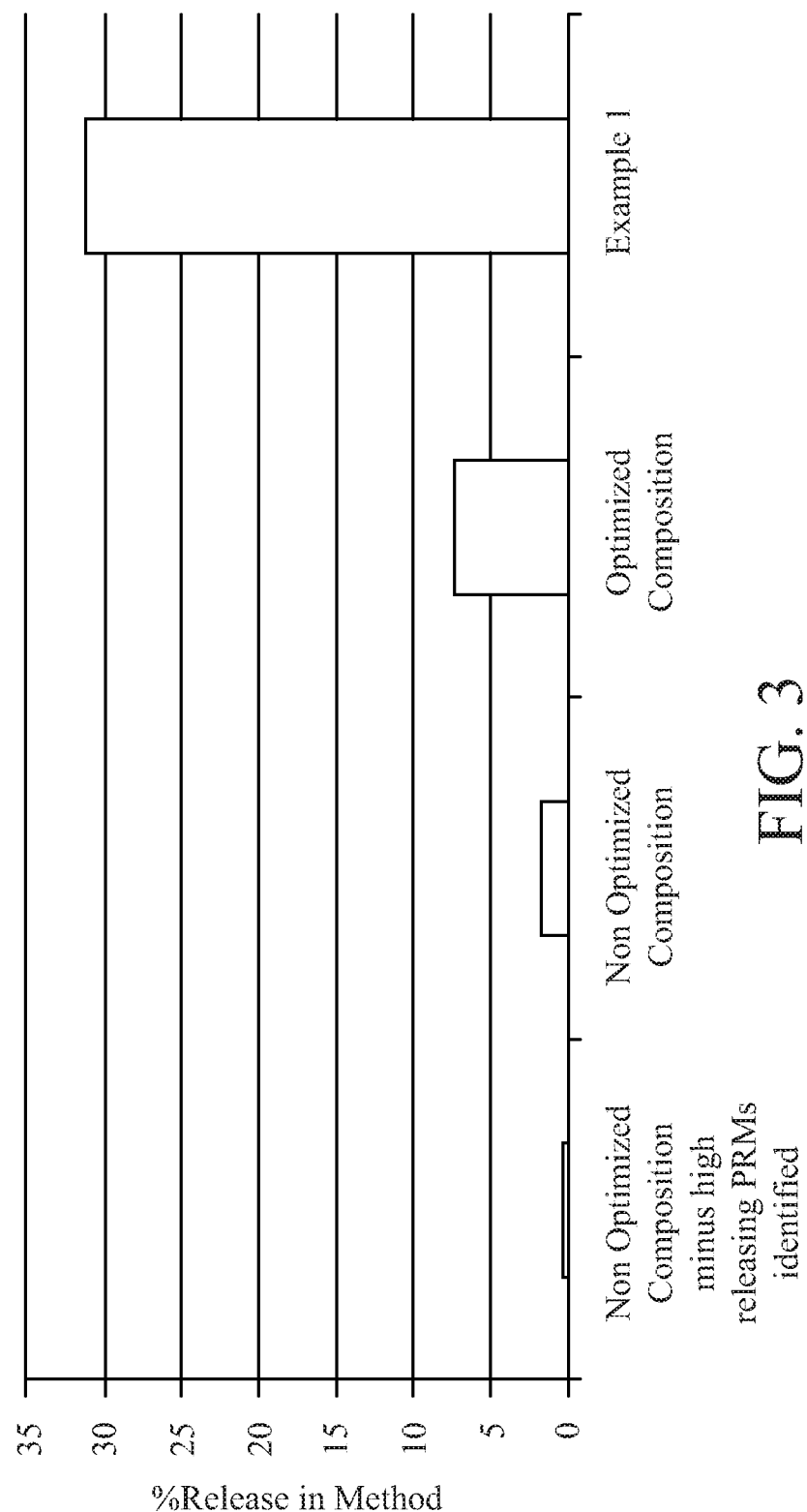
FIG. 3 is a graph showing the percentage of perfume complexed with a beta cyclodextrin that is released when measured in accordance with the In Vitro Perfume Release Method.

An understanding of what is and what isn't releasing from a cyclodextrin could help to improve the efficacy of the cyclodextrin complex. Since less than 5% of the perfumes used in a cyclodextrin complex were efficiently releasing from the cyclodextrin complex (see FIG. 3, Non Optimized Composition), the perfume raw materials that were being released from the cyclodextrins were identified to determine if there were characteristics common among them which could be used to help develop a perfume for optimized released from a cyclodextrin.

With water being the key releasing agent, it was found that perfume raw materials with more affinity with water (lower log P) had better release from the cyclodextrin complex. Perfume raw materials with a lower cyclodextrin complex stability constant (log k) also had better release from a cyclodextrin complex. In addition, a lower molecular weight, which may correlate with a lower cyclodextrin complex stability constant, also correlates with a better release. To demonstrate these characteristics as impacting the release from the cyclodextrin complex, new perfumes were created. One perfume removed these higher releasing perfume materials from the original low release perfume as a negative control check (see FIG. 3, Non Optimized Composition minus high releasing PRM's identified vs. Non Optimized Composition). In release testing, the Non Optimized Composition minus the high releasing PRM's had less than one third of the release of the original Non Optimized Composition (see FIG. 3).

An optimized perfume was then made which utilized about 70%, by weight of the perfume, of perfume raw materials with a log P, stability constant, and weight average molecular weight believed to help with perfume release from a cyclodextrin complex. This perfume, Optimized Composition from FIG. 3, had 4 times the release of the original composition (Non Optimized Composition). Another perfume was made with 100% of the perfume matching these physical property characteristics (Example 1). This perfume had over 15 times the release of the Non Optimized Composition.

As noted above, one of the characteristics of a perfume raw material that can impact its release from a cyclodextrin is its complex stability constant. This signifies how strongly the perfume raw material binds with the cyclodextrin. While a minimum complex stability constant allows for the perfume raw material to bind and stay bound, at some point the affinity of the perfume raw material for the cyclodextrin can become so strong that it becomes difficult to release. It is believed that a complex stability constant of more than 3 can interfere with the release of the perfume raw material upon a triggering event. This is not to say that perfume raw materials with a complex stability constant above 3 cannot be used, just that the ability to release such materials should be taken into consideration during perfume design. For example, FIG. 1 shows the binding complex of perfume raw materials in a perfume. The graph on the left shows the make-up of a more typical perfume, while the graph on the right shows a perfume after optimization for release from a cyclodextrin. The optimized formula showed an improvement of 15 times over Non Optimized Perfume A.

Figure 2:
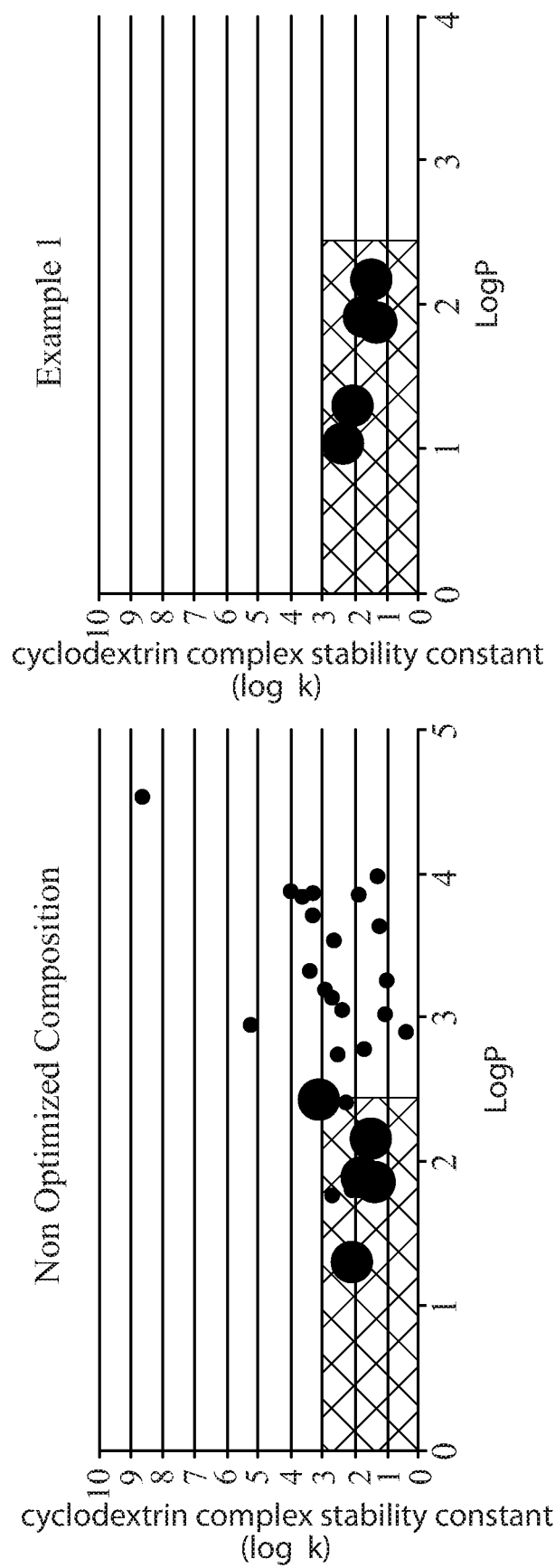
FIG. 2 is a side-by-side comparison of the cyclodextrin complex stability constant over Log P of a perfume before and after optimization for release from a cyclodextrin complex.

Another property of a perfume raw material which can impact its ability to release from a cyclodextrin is its ClogP. ClogP is the calculation of the log P value of a compound, which is the logarithm of its partition coefficient between n-octanol and water ($C_{octanol}/C_{water}$). Thus, log P, or if calculated cLogP, is a measure of a perfume raw material's hydrophilicity. High log P values correspond to low hydrophilicities. It is believed that a low log P, i.e., higher affinity for water, can positively impact the release of a perfume raw material from a cyclodextrin upon appropriate contact with moisture. For example, FIG. 2 shows the binding complex of perfume raw materials in a perfume and the ClogP. The graph on the left shows the make-up of a more typical perfume, while the graph on the right shows a perfume after optimization for release from a cyclodextrin. The optimized formula showed an improvement of 15 times over the Non Optimized Composition. For this application, it is believed a ClogP value of about 2.5 or less is optimal for release from a cyclodextrin complex.

A third property that can impact the release of a perfume raw material from a cyclodextrin is its weight average molecular weight. It is believed that perfume raw materials which are smaller in size will have less binding points to a cyclodextrin and thus are more easily released. Ideally, a perfume raw material for optimal release will have a weight average molecular weight of about 200 Daltons or less.

A fourth property that can impact the need for efficacy is the odor detection threshold. Odor detection threshold is the minimum level at which a perfume raw material can be detected by the average human nose. For a perfume raw material with a low odor detection threshold, less of the perfume raw material needs to be released from a cyclodextrin in order for the perfume raw material to be noticed. This feature can allow for the use of perfume raw materials which would otherwise be seen as too difficult to release en masse from a cyclodextrin. Optimally, the odor detection threshold of a perfume raw material is about 7-log molar concentration or more.

Figure 4:
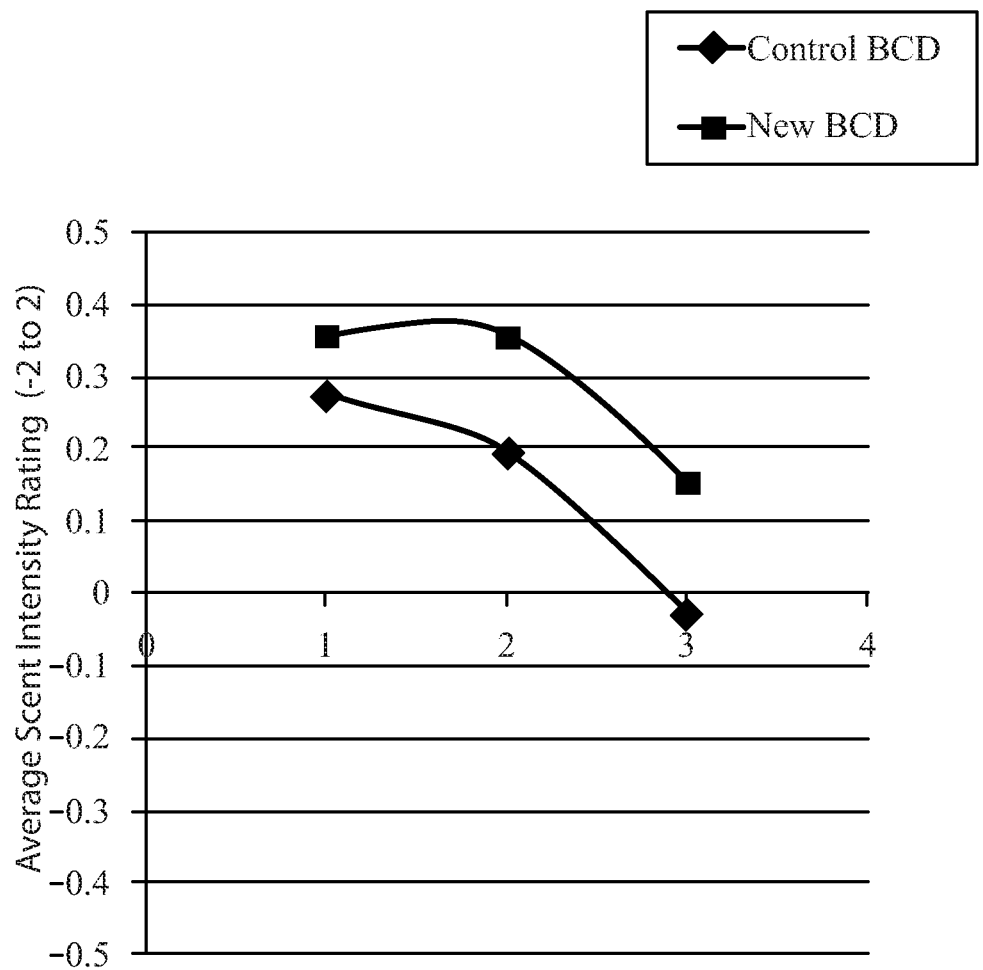
FIG. 4 is a graph showing the average scent intensity at each assessment time point, where 1 is at application, 2 is during the day, and 3 is at the end of the day.

To determine whether the release enhancement was noticeable to consumers, an optimized cyclodextrin complex was tested against an in-market complex with less than 5% release. The products were given to over 90 consumers each to wear directly on their skin every day for 2 weeks. After the 2 weeks they were asked to rate the intensity of the fragrance on a scale of −2 (much too weak) to 2 (much too strong). They rated the product they wore at application, during the day, and at the end of the day. FIG. 4 shows on average those who wore a topically applied skin product with the optimized cyclodextrin complex (designed as "New BCD") reported a higher fragrance intensity at each time point evaluated versus a control cyclodextrin complex (designated as "Control BCD").

Cyclodextrin particles and cyclodextrin complexes comprising a perfume raw material can be formed by various methods. For example, a solvent (e.g., water), unloaded cyclodextrin particles, and a perfume raw material can be placed into a container and then mixed for a period of time to permit loading of perfume molecules into "cavities" of cyclodextrin molecules. The mixture may or may not be processed further; e.g., processed through a colloid mill and/or homogenizer. The solvent is then substantially removed, like by drying, from the resulting mixture or slurry to yield cyclodextrin complex particles. Different manufacturing techniques may, however, impart different particle/complex characterizations, which may or may not be desirable in the product. The particles and/or complexes can have a low level of moisture prior to their inclusion into a product. For example, some may have a moisture level of less than about 20% by weight of the particles, less than about 10% by weight of the particles, or even less than about 6% by weight of the particles, prior to the inclusion of the volume of particles into a composition. Other moisture levels may also be suitable.

Spray drying a slurry or mixture of cyclodextrin complex that includes perfume is one manufacturing technique capable of producing the cyclodextrin particles and cyclodextrin complexes having the above-noted, low moisture levels. Table I below provides a comparison of spray dried cyclodextrin complexes versus complexes formed via an extruder process (kneading).

TABLE I

| Cyclodextrin Complex Moisture Level | |
|---|---|
| Sample | % Moisture |
| Spray Dry Process Sample A | 4.4 |
| Spray Dry Process Sample B | 3.7-4.5 |
| Spray Dry Process Sample C | 5.3 |
| Extruder Process Sample A | 27.87 |
| Extruder Process Sample B | 27.97 |
| Extruder Process Sample C | 24.00 |

Water content, USP (United States Pharmacopeia, current as of Aug. 1, 2006) <921> Method I is the analytical method for determining cyclodextrin complex moisture level, as shown in Table I.

As one can see from Table 1, the moisture level directly manifested by these two methods is dramatically different. It should be understood that this comparison is not intended to disclaim kneading/extruder processes from appended claims that do not specify a particular complex formation process. Rather, a kneading and extrusion method, or other method forming particles/complexes with higher than desired moisture levels, could utilize additional processing after their initial formation. For example, extruded complexes may be processed through an oven or dryer, or exposed to a controlled environment for a period of time.

Although not wishing to be bound by theory, it is believed that cyclodextrin particles/complexes having a relatively high moisture level have an increased tendency to agglomerate. The agglomerated particles may reach a size that is perceptible by a consumer; that is, a consumer may characterize the composition as being "gritty", which may be undesirable. Microbial growth is another potential disadvantage associated with employing cyclodextrin particles/complexes with relatively high moisture levels into a final composition depending on the remaining ingredients of the composition and/or storage parameters.

The efficiency or level of complexing with a perfume is another parameter of cyclodextrin complexes that can vary greatly depending on the manufacturing techniques employed. Put another way, the percent of perfume that is associated with the interior of a cyclodextrin molecule compared to the percent of perfume that is associated with the exterior of the cyclodextrin complex. The perfume that is on the exterior region of the complex is essentially free to be expressed without the requirement of a triggering mechanism. The probability that a consumer perceives the perfume prior to a triggering mechanism increases as the level of free fragrance increases. Such perception of a perfume prior to a triggering mechanism may not be desired depending on the overall composition design and targeted benefit associated with employment of the cyclodextrin complexes. The percent of perfume that is complexed with cyclodextrin can be, for example, greater than about 75%, in some instances greater than about 90%, and in other instances greater than about 95%. It should be understood that these levels of perfume complexation are directly associated with the complex formation process itself; the percentages do not represent a formulation design of adding a first percentage of perfume via a cyclodextrin complex and adding a second percentage of neat perfume or perfume raw material.

Spray drying a slurry or mixture of cyclodextrin-fragrance complexes is one manufacturing technique capable of producing cyclodextrin complexes having the above-noted levels of fragrance complexation. Table II below provides a comparison of spray dried cyclodextrin complexes versus complexes formed via an extruder process (kneading).

TABLE II

Percent of Fragrance Loading in Cyclodextrin Complexes

| Sample | Complexation Efficiency |
|---|---|
| Spray Dry Process Sample A | 96.6 |
| Spray Dry Process Sample B | 96.8 |
| Spray Dry Process Sample C | 96.2 |
| Extruder Process Sample A | 60.77 |
| Extruder Process Sample B | 65.47 |
| Extruder Process Sample C | 67.07 |

One can see from Table II that spray drying is capable of producing cyclodextrin complexes with very little free fragrance as compared to a kneading/extruder process. The skilled artisan should appreciate that the comparison provided in Table II is not intended to disclaim kneading/extruder processes from appended claims that do not specify a particular complex formation process. Rather, additional processing steps may, for example, be employed to eliminate free fragrance associated with extruded complexes prior to their inclusion into a composition.

The analytical method for determining the percent of fragrance complexed, as shown in Table II, determines the free fragrance level in the complex by dissolving a sample in tetrahydrofuran (THF) adding an internal standard, and analyzing by capillary gas chromatography (GC). The complexed fragrance level is measured by extracting the same sample in acetone containing an internal standard, and analyzing by GC.

Complexation Efficiency=% Complexed/[% Complexed+% Free]

The cyclodextrin complexes may be coated to minimize premature release/activation. Generally, any material that is capable of resisting water penetration is suitable. The coating material may include, for example, hydrocarbons, waxes, petrolatum, silicones, silicone derivatives, partially or fully esterified sucrose esters, and polyglycerol esters. Using petrolatum as an example, a coating process may include combining cyclodextrin complexes with petrolatum at a ratio of about 1:1, for example, and then mixing until the complexes are satisfactorily coated.

Perfumes

The perfume comprises perfume raw materials. At least a portion of the perfume raw materials may have a cyclodextrin binding coefficient of about 3.0 or less; about 2.5 or less, about 2.0 or less, about 1.0 or less, to about −2. Some of the perfume raw material may have a cLogP of about 2.5 or less, about 2.0 or less, about 1.5 or less, about 1.0 or less, to about −3. Some of the perfume raw materials may have a weight average molecular weight of about 200 Daltons or less, about 180 Daltons or less, about 150 Daltons or less, about 100 Daltons or less, to about 50 Daltons. The perfume raw materials will have an odor detection threshold. At least a portion of the perfume raw materials in a perfume will have an odor detection threshold of about 7–log molar concentration or greater; about 8–log molar concentration or greater; about 9–log molar concentration or greater; to about 11.5–log molar concentration.

The perfume comprises about 10% or more, by weight of the perfume, of perfume raw materials which have a cyclodextrin binding coefficient of about 3.0 or less, a cLogP of about 2.5 or less, and a weight average molecular weight of about 200 Daltons or less. Going further, the perfume may comprise about 20% or more; about 30% or more; about 40% or more, or about 50% or more, up to 100%; of perfume raw materials which have a cyclodextrin binding coefficient of about 3.0 or less, a cLogP of about 2.5 or less, and a weight average molecular weight of about 200 Daltons or less. In addition, a perfume may also include perfume raw materials with an odor detection threshold of about 7–log molar concentration.

A representative, non-limiting, list of perfume raw materials that have a cyclodextrin binding coefficient of about 3.0 or less, a cLogP of about 2.5 or less, and a weight average molecular weight of about 200 Daltons or less is included in the chart below.

| CAS Number | Name | LogP (v3.0) | Formula Weight | Odor Detection Threshold, Neural Net model | bCD Complex Stability Constant |
|---|---|---|---|---|---|
| 10031-96-6 | eugenyl formate | 2.35 | 192.21 | 8.84 | 2.71 |
| 100-52-7 | Benzaldehyde | 1.4 | 106.12 | 7.45 | 2.19 |
| 10094-40-3 | 2-hexen-1-yl acetate | 2.21 | 142.20 | 8.20 | 1.45 |
| 101-39-3 | alpha-methyl cinnamaldehyde | 2.18 | 146.19 | 8.83 | 1.08 |
| 101-41-7 | Methyl phenylacetate | 1.89 | 150.18 | 8.02 | 2.14 |
| 101-48-4 | Viridine (PADMA) | 1.65 | 166.22 | 8.01 | 2.26 |
| 101-97-3 | Ethyl 2-phenylacetate | 2.39 | 164.20 | 8.63 | 2.25 |
| 103-25-3 | methyl hydrocinnamate | 2.04 | 164.20 | 8.20 | 2.24 |
| 103-26-4 | Methyl cinnamate | 2.44 | 162.19 | 8.97 | 2.07 |
| 103-45-7 | 2-Phenylethyl acetate | 2.07 | 164.20 | 8.15 | 1.54 |
| 103-54-8 | Cinnamyl acetate | 2.49 | 176.22 | 8.51 | 1.53 |
| 104-09-6 | lilac acetaldehyde | 2.12 | 134.18 | 9.36 | 2.67 |
| 104-20-1 | 4-(p-Methoxyphenyl)-2-butanone (frambinone) | 1.88 | 178.23 | 8.86 | 1.72 |
| 104-46-1 | Anethole | 2.43 | 148.20 | 8.79 | 2.34 |
| 104-50-7 | gamma-Octalactone | 2.06 | 142.20 | 8.30 | 2.94 |
| 104-53-0 | 3-phenyl propionaldehyde | 1.65 | 134.18 | 8.95 | 2.47 |
| 104-54-1 | Cinnamic alcohol | 1.68 | 134.18 | 8.58 | 2.15 |
| 104-55-2 | Cinnamic aldehyde | 1.92 | 132.16 | 8.56 | 2.37 |
| 104-62-1 | Phenethyl formate | 1.82 | 150.18 | 8.10 | 2.32 |
| 104-64-3 | 3-phenyl propyl formate | 2.22 | 164.20 | 8.51 | 2.46 |
| 105-01-1 | Isobutyl furylpropionate | 2.34 | 196.25 | 8.60 | 2.30 |
| 10521-96-7 | Styryl acetate | 2.3 | 162.19 | 8.60 | 1.47 |
| 105-86-2 | geranyl formate | 2.44 | 182.26 | 8.49 | −1.85 |
| 10606-47-0 | 3-Hepten-1-ol | 1.79 | 114.19 | 8.47 | 2.11 |
| 106-22-9 | Citronellol | 2.49 | 156.27 | 8.37 | −0.64 |
| 106-24-1 | trans-Geraniol | 1.95 | 154.25 | 9.36 | −2.13 |
| 106-25-2 | Nerol | 1.95 | 154.25 | 9.36 | −2.13 |
| 106-26-3 | Neral | 2.33 | 152.24 | 8.48 | −1.82 |
| 106-72-9 | melon heptenal (melonal) | 2.09 | 140.23 | 8.09 | −0.64 |
| 107-03-9 | Propyl mercaptan | 1.87 | 76.16 | 9.04 | 0.65 |
| 1073-26-3 | 2-Propionylpyrrole | 1.37 | 123.15 | 8.13 | 1.88 |
| 110458-85-0 | 5,6-Dimethyl-1-(1-methylethenyl)bicyclo[2.2.1]hept-5-ene-2-methanol | 2.36 | 192.30 | 9.46 | 1.27 |
| 1123-85-9 | Hydratopic alcohol | 1.85 | 136.19 | 8.19 | 1.99 |
| 1131-62-0 | 3,4-Dimethoxyacetophenone | 1.7 | 180.20 | 8.15 | 1.63 |
| 116-26-7 | Safranal | 2.4 | 150.22 | 8.54 | 1.30 |
| 118-93-4 | 2-Hydroxyacetophenone | 1.97 | 136.15 | 8.15 | 1.38 |
| 1197-06-4 | cis-carveol | 1.86 | 152.24 | 8.60 | 0.32 |
| 1205-17-0 | ocean propanal (helional) | 1.77 | 192.21 | 8.89 | 2.67 |
| 120-58-1 | Isosafrol | 2.01 | 162.19 | 8.45 | 2.52 |
| 120-72-9 | Indole | 2.34 | 117.15 | 8.20 | 2.19 |
| 120-75-2 | 2-Methylbenzothiazole | 2.14 | 149.21 | 8.12 | 2.83 |
| 121-32-4 | Ethyl vanillin | 1.53 | 166.18 | 10.32 | 2.41 |
| 121-33-5 | Vanillin | 1.04 | 152.15 | 9.93 | 2.36 |
| 121-98-2 | Methyl p-anisate | 1.99 | 166.18 | 8.54 | 2.05 |
| 122-63-4 | Benzyl propionate | 2.24 | 164.20 | 8.29 | 2.01 |
| 122-72-5 | 3-phenyl propyl acetate | 2.48 | 178.23 | 8.70 | 1.73 |
| 122-78-1 | phenyl acetaldehyde | 1.46 | 120.15 | 8.40 | 2.30 |
| 123-08-0 | p-Hydroxybenzaldehyde | 1.29 | 122.12 | 9.34 | 2.28 |
| 123-11-5 | para-anisaldehyde | 1.53 | 136.15 | 7.72 | 2.29 |
| 123-92-2 | Isoamyl acetate | 1.87 | 130.19 | 7.12 | 1.33 |
| 13327-56-5 | Ethyl 3-methylthiopropionate | 1.47 | 148.22 | 8.09 | 1.88 |
| 134-20-3 | Methyl anthranilate | 1.58 | 151.17 | 8.22 | 1.69 |
| 13494-08-1 | 1,2-Cyclopentanedione, 3-ethyl- | 0.5 | 126.16 | 8.29 | 2.72 |
| 134-96-3 | Syringaldehyde | 0.94 | 182.18 | 9.89 | 2.48 |
| 13678-68-7 | furfuryl thioacetate | 1.09 | 156.20 | 8.11 | 1.33 |
| 13679-85-1 | blackberry thiophenone | 0.73 | 116.18 | 8.44 | 2.06 |
| 140-39-6 | p-Cresyl acetate | 2.17 | 150.18 | 8.10 | 1.67 |
| 14049-11-7 | linalool oxide (pyranoid) | 1.89 | 170.25 | 8.45 | 2.62 |
| 141-27-5 | Geranial | 2.33 | 152.24 | 8.48 | −1.82 |
| 142653-61-0 | Parmanyl | 1.75 | 153.22 | 8.13 | 2.05 |
| 142-83-6 | Sorbinaldehyde | 1.29 | 96.13 | 8.57 | 2.29 |
| 14360-50-0 | Pentyl 2-furyl ketone | 2.49 | 166.22 | 9.39 | 2.44 |
| 150-19-6 | m-Guaiacol | 1.39 | 124.14 | 8.16 | 2.02 |
| 1504-55-8 | alpha-Methylcinnamic alcohol (cypriol) | 1.73 | 148.20 | 8.68 | 0.74 |
| 15111-56-5 | Ethyl cyclohex-3-enecarboxylate | 1.86 | 154.21 | 8.47 | 2.78 |
| 1516-17-2 | 2,4-Hexadienyl acetate | 1.75 | 110.16 | 8.30 | 1.36 |
| 15174-69-3 | 4-Hydroxy-3-methylbenzaldehyde | 1.63 | 136.15 | 10.25 | 2.24 |
| 15186-51-3 | Furan, 3-methyl-2-(3-methyl-2-butenyl)- | 2.04 | 150.22 | 8.26 | −0.46 |
| 1540-28-9 | n-Pentyl acetoacetate | 1.63 | 172.22 | 8.04 | 1.79 |
| 1552-67-6 | Ethyl 2-hexenoate | 2.49 | 142.20 | 8.30 | 2.12 |

| CAS Number | Name | LogP (v3.0) | Formula Weight | Odor Detection Threshold, Neural Net model | bCD Complex Stability Constant |
|---|---|---|---|---|---|
| 15679-12-6 | 2-Ethyl-4-methylthiazole | 1.69 | 127.20 | 8.31 | 2.13 |
| 15679-13-7 | tropical thiazole | 2.12 | 141.23 | 8.25 | 2.33 |
| 16251-77-7 | Trifernal | 2.28 | 148.20 | 8.87 | 2.51 |
| 1646-26-0 | Coumarone | 1.9 | 160.17 | 8.64 | 1.90 |
| 16491-25-1 | 2,4-Hexadienyl propionate | 2.44 | 154.21 | 8.72 | 1.97 |
| 1679-07-8 | Cyclopentyl mercaptan | 2.24 | 102.19 | 9.09 | 1.47 |
| 1679-09-0 | 2-Methyl-2-butanethiol | 2.45 | 104.21 | 9.16 | 0.79 |
| 16957-70-3 | trans-2-Methyl-2-pentenoic acid (Strawberriff) | 1.33 | 114.14 | 8.78 | 0.65 |
| 1708-34-5 | 2-Hexyl-1,3-dioxolane | 2.17 | 158.24 | 8.11 | 2.56 |
| 1708-81-2 | cis-3-Hepten-1-ol | 1.79 | 114.19 | 8.47 | 2.11 |
| 1708-82-3 | 3-Hexenyl acetate | 2.18 | 142.20 | 8.16 | 1.48 |
| 17102-64-6 | Trans,trans-2,4-Hexadien-1-01 | 0.96 | 98.14 | 8.22 | 2.06 |
| 1754-62-7 | Methyl Trans-Cinnamate, 99% | 2.44 | 162.19 | 8.97 | 2.07 |
| 1759-28-0 | 4-Methyl-5-vinylthiazole | 1.51 | 125.19 | 8.56 | 1.62 |
| 17626-75-4 | 2-Propylthiazole | 1.51 | 127.20 | 8.23 | 1.79 |
| 18031-40-8 | (S),(−)-Perillaaldehyde | 2.34 | 150.22 | 9.80 | 1.85 |
| 18277-27-5 | 2-(1-Methylpropyl)thiazole | 1.9 | 141.23 | 8.25 | 1.71 |
| 18479-68-0 | (+)-P-Menth-1-en-9-ol, 97%, mixture of isomers | 2.26 | 154.25 | 8.87 | 1.66 |
| 18640-74-9 | Isobutyl thiazole | 1.92 | 141.23 | 8.29 | 2.02 |
| 18829-55-5 | trans-2-Heptenal | 2.1 | 112.17 | 8.76 | 2.33 |
| 18881-04-4 | (1S)-(−)-cis-Verbenol | 2.03 | 152.24 | 8.09 | 2.61 |
| 189440-77-5 | Anapear | 2.3 | 154.21 | 8.78 | 2.20 |
| 1901-38-8 | alpha-Campholenic alcohol | 2.03 | 154.25 | 8.08 | 1.32 |
| 19788-49-9 | Ethyl 2-mercaptopropionate | 1.41 | 134.19 | 8.39 | 0.99 |
| 19819-98-8 | 2-Methylphenethyl alcohol | 1.66 | 136.19 | 8.46 | 2.36 |
| 2046-17-5 | Methyl 4-phenylbutyrate | 2.46 | 178.23 | 8.75 | 2.37 |
| 20474-93-5 | Allyl crotonate | 1.63 | 126.16 | 8.29 | 2.24 |
| 2051-78-7 | Allyl butyrate | 1.88 | 128.17 | 8.17 | 2.21 |
| 2051-96-9 | Benzyl lactate | 1.35 | 180.20 | 8.15 | 1.70 |
| 20665-85-4 | Vanillin isobutyrate | 1.92 | 222.24 | 8.20 | 2.20 |
| 2111-75-3 | perillaldehyde | 2.34 | 150.22 | 9.80 | 1.85 |
| 2142-94-1 | Neryl Formate | 2.44 | 182.26 | 8.49 | −1.85 |
| 2179-58-0 | Allyl methyl disulfide | 1.9 | 120.23 | 8.59 | 1.44 |
| 2179-60-4 | Methyl propyl disulfide | 2.28 | 122.24 | 8.56 | 1.97 |
| 21835-00-7 | 2-Cyclopenten-1-one, 2-hydroxy-3,4-dimethyl- | −0.02 | 126.16 | 8.91 | 0.76 |
| 21835-01-8 | 3-Ethyl-2-hydroxy-2-cyclopenten-1-one | 0.06 | 126.16 | 8.79 | 2.41 |
| 22104-78-5 | 2-Octenol-1 | 2.27 | 128.21 | 8.81 | 2.24 |
| 2217-33-6 | Tetrahydrofurfuryl butyrate | 1.54 | 172.22 | 8.40 | 2.22 |
| 22451-63-4 | Allo-ocimenol | 2.42 | 152.24 | 8.51 | −0.99 |
| 22460-95-3 | 7-Octene-1,6-diol, 3,7-dimethyl- | 1.33 | 172.27 | 8.27 | 0.79 |
| 22924-15-8 | 3-Ethoxybenzaldehyde | 1.99 | 150.18 | 8.14 | 2.33 |
| 22927-13-5 | 2-Ethylbenzaldehyde | 2.06 | 134.18 | 8.78 | 2.53 |
| 2305-21-7 | 2-hexen-1-ol | 1.3 | 100.16 | 8.09 | 2.06 |
| 23495-12-7 | Phenoxyethyl propionate | 2.43 | 194.23 | 8.92 | 1.78 |
| 23911-56-0 | Nerolione | 2.02 | 174.20 | 8.74 | 2.04 |
| 2445-83-2 | 7-Methylcoumarin | 2.42 | 160.17 | 8.79 | 2.78 |
| 2463-63-0 | Butylacrolein | 2.1 | 112.17 | 8.76 | 2.33 |
| 2497-18-9 | 2-Hexen-1-yl acetate | 2.21 | 142.20 | 8.20 | 1.45 |
| 2555-49-9 | Ethyl phenoxyacetate | 2.04 | 180.20 | 8.36 | 1.93 |
| 26553-46-8 | Ethyl trans-3-hexenoate | 2.25 | 142.20 | 8.34 | 2.14 |
| 8/6/2719 | N-Acetyl methyl anthranilate | 1.21 | 193.20 | 8.00 | 1.48 |
| 27829-72-7 | Ethyl trans-2-hexenoate | 2.49 | 142.20 | 8.30 | 2.12 |
| 27939-60-2 | Vertoliff (triplal extra) | 1.8 | 138.21 | 9.24 | 1.71 |
| 28069-72-9 | (2E,6Z)-Nona-2,6-dien-1-ol | 2.43 | 140.23 | 9.59 | 2.24 |
| 28977-58-4 | Ocimenol | 2.02 | 152.24 | 8.71 | −0.59 |
| 29414-56-0 | 2,6-Dimethyl-1,5,7-octatrienol-3 | 1.96 | 152.24 | 8.89 | −0.76 |
| 29548-14-9 | p-Menth-1-ene-9-ol | 2.24 | 152.24 | 9.40 | 1.85 |
| 30361-28-5 | 2,4-Octadien-1-al | 2.45 | 124.18 | 9.33 | 2.32 |
| 30954-98-4 | Propyl anthranilate | 2.47 | 179.22 | 8.88 | 1.87 |
| 3194-17-0 | 2-Pentanoylfuran | 1.99 | 152.19 | 8.97 | 2.40 |
| 32272-48-3 | 4-Ethyl-2-methylthiazole | 1.7 | 127.20 | 8.32 | 2.25 |
| 32764-98-0 | Jasmolactone | 2.36 | 168.24 | 8.72 | 2.96 |
| 33467-73-1 | cis-3-Hexenyl formate | 1.69 | 128.17 | 8.22 | 2.25 |
| 3391-86-4 | 1-Octenol-3 | 2.36 | 128.21 | 8.29 | 2.19 |
| 3581-91-7 | 4,5-Dimethylthiazole | 0.91 | 113.18 | 8.10 | 1.30 |
| 3583-00-4 | 4,4-Dimethyl-5-isopropyl-1,3-dioxolane | 1.92 | 158.24 | 8.99 | 1.98 |

-continued

| CAS Number | Name | LogP (v3.0) | Formula Weight | Odor Detection Threshold, Neural Net model | bCD Complex Stability Constant |
|---|---|---|---|---|---|
| 35926-04-6 | 1-Hexen-3-yl acetate | 2.31 | 142.20 | 8.02 | 1.68 |
| 36701-01-6 | Furfuryl valerate | 1.89 | 182.22 | 8.39 | 2.12 |
| 36806-46-9 | 2,6-Dimethyl-6-hepten-1-ol | 2.4 | 142.24 | 8.07 | 0.76 |
| 3681-71-8 | cis-3-Hexenyl acetate | 2.18 | 142.20 | 8.16 | 1.48 |
| 3681-82-1 | trans-3-Hexenyl acetate | 2.18 | 142.20 | 8.16 | 1.48 |
| 36880-33-8 | 5-Ethyl-2-thiophenecarbaldehyde | 1.85 | 140.20 | 8.19 | 2.64 |
| 37973-51-6 | 2-Phenyl-1(2)propenyl-1 ester | 2.47 | 176.22 | 8.82 | 0.44 |
| 38142-45-9 | 3-Cyclohexene-1-ethanol, 4-methyl-.beta.-methylene-, (R)- | 1.84 | 152.24 | 8.62 | 1.58 |
| 39252-02-3 | Furfuryl hexanoate | 2.38 | 196.25 | 8.80 | 2.17 |
| 39677-52-6 | 3-Methoxy Cinnamaldehyde | 1.86 | 162.19 | 8.84 | 2.49 |
| 40010-99-9 | 3-Acetyl-5-butyldihydro-2(3H)-furanone | 1.71 | 184.24 | 8.57 | 2.58 |
| 40790-29-2 | Pyrazine, 3-butyl-2,5-dimethyl- | 2.29 | 164.25 | 8.18 | 2.48 |
| 409-02-9 | Methyl Heptenone | 2.27 | 126.20 | 8.58 | 2.38 |
| 4175-66-0 | 2,5-Dimethylthiazole | 0.94 | 113.18 | 8.08 | 1.63 |
| 4180-23-8 | (E)-anethol | 2.43 | 148.20 | 8.79 | 2.34 |
| 41847-88-5 | Phenylethyl oxy-acetaldehyde | 1.55 | 164.20 | 8.61 | 2.34 |
| 42348-12-9 | 3-Ethyl-2-hydroxy-4-methylcyclopent-2-en-1-one | 0.54 | 140.18 | 9.10 | 2.58 |
| 3/5/4313 | (E,E)-2,4-heptadien-1-al | 1.98 | 110.16 | 9.00 | 2.29 |
| 6/1/4364 | Cinnamic aldehyde dimethyl acetal | 2.02 | 178.23 | 8.44 | 2.03 |
| 4501-58-0 | Campholene aldehyde | 2.2 | 152.24 | 8.31 | 1.43 |
| 4634-89-3 | cis-4-Hexenal | 1.05 | 98.14 | 9.24 | 2.26 |
| 4643-25-8 | 2-Hepten-4-one | 1.85 | 112.17 | 8.31 | 2.21 |
| 4643-27-0 | 2-Octen-4-one | 2.42 | 126.20 | 8.70 | 2.43 |
| 473-67-6 | Verbenol | 2.03 | 152.24 | 8.09 | 2.61 |
| 4748-78-1 | 4-Ethylbenzaldehyde | 2.39 | 134.18 | 9.19 | 2.54 |
| 491-04-3 | Piperitol | 2.4 | 154.25 | 8.70 | 1.72 |
| 491-09-8 | piperitenone | 2.33 | 150.22 | 8.40 | −1.20 |
| 491-31-6 | Isocoumarin | 1.69 | 146.15 | 8.63 | 2.45 |
| 491-35-0 | Lepidine | 2.46 | 143.19 | 8.13 | 2.44 |
| 11/8/4940 | ethyl maltol | 0.17 | 140.14 | 7.44 | 1.94 |
| 496-77-5 | Butyroin | 1.29 | 144.21 | 8.36 | 2.22 |
| 499-44-5 | Hinokitiol | 1.35 | 164.20 | 9.32 | 2.71 |
| 50888-63-6 | Pyrazine, 2-butyl-3,5-dimethyl- | 2.3 | 164.25 | 8.19 | 2.27 |
| 53046-97-2 | cis-3, cis-6-nonadienol | 2.45 | 140.23 | 9.52 | 2.16 |
| 53398-78-0 | trans-2-Hexenyl formate | 1.71 | 128.17 | 8.31 | 2.23 |
| 53399-81-8 | Ethyl 2-methyl-4-pentenoate | 2.26 | 142.20 | 8.16 | 2.08 |
| 536-50-5 | 1-(4-Methylphenyl)ethanol | 2 | 136.19 | 8.07 | 2.39 |
| 536-59-4 | Perillyl alcohol | 1.83 | 152.24 | 8.58 | 1.69 |
| 536-60-7 | Cumic alcohol | 2.39 | 150.22 | 8.68 | 2.39 |
| 5392-40-5 | Citral | 2.33 | 152.24 | 8.48 | −1.82 |
| 5396-89-4 | Benzyl acetoacetate | 1.43 | 192.21 | 8.05 | 1.45 |
| 12/2/5406 | p-Methylhydrocinnamic aldehyde | 2.19 | 148.20 | 9.57 | 2.84 |
| 541-58-2 | 2,4-Dimethylthiazole | 1.24 | 113.18 | 8.08 | 1.89 |
| 5426-78-8 | Acetaldehyde phenyl ethyl acetal | 2.22 | 166.22 | 8.56 | 1.83 |
| 6/6/5462 | Canthoxal | 2.16 | 178.23 | 8.80 | 2.49 |
| 6/8/5466 | Ethyl 3-mercaptopropionate | 1.36 | 134.19 | 8.92 | 1.25 |
| 5471-51-2 | Raspberry ketone | 1.58 | 164.20 | 7.67 | 1.70 |
| 554-14-3 | 2-Methylthiophene | 2.06 | 98.16 | 8.11 | 1.52 |
| 55722-59-3 | 3,6-Octadienal, 3,7-dimethyl- | 2.34 | 152.24 | 8.51 | −1.89 |
| 5577-44-6 | 2,4-Octadienal | 2.45 | 124.18 | 9.33 | 2.32 |
| 5660-60-6 | Cinnamaldehyde ethylene glycol acetal | 2.15 | 176.22 | 8.04 | 2.16 |
| 56805-23-3 | trans-3, cis-6-nonadienol | 2.45 | 140.23 | 9.52 | 2.16 |
| 57266-86-1 | 2-Heptenal, (2Z)- | 2.1 | 112.17 | 8.76 | 2.33 |
| 57500-00-2 | Methyl furfuryl disulfide | 1.92 | 160.25 | 8.19 | 2.38 |
| 579-74-8 | o-Acetylanisole | 1.55 | 150.18 | 8.40 | 1.56 |
| 58461-27-1 | Lavandulol | 1.95 | 154.25 | 8.98 | −1.82 |
| 585-74-0 | 3-Methylacetophenone | 2.27 | 134.18 | 8.23 | 1.65 |
| 589-18-4 | p-Tolyl alcohol | 1.62 | 122.17 | 8.01 | 2.35 |
| 59020-85-8 | Furfuryl thiopropionate | 1.61 | 170.23 | 8.45 | 2.16 |
| 59021-02-2 | 2-Mercaptomethylpyrazine | 0.34 | 126.18 | 8.26 | 0.66 |
| 5910-85-0 | 2,4-Heptadienal | 1.98 | 110.16 | 9.00 | 2.29 |
| 5912-86-7 | cis-iso-Eugenol | 1.85 | 164.20 | 8.60 | 2.38 |
| 5925-68-8 | S-Ethyl benzothioate | 2.21 | 152.21 | 8.74 | 1.83 |
| 5932-68-3 | trans-Isoeugenol | 1.85 | 164.20 | 8.60 | 2.38 |
| 606-27-9 | Methyl 2-nitrobenzoate | 1.57 | 181.15 | 8.45 | 2.25 |
| 606-45-1 | Methyl o-methoxybenzoate | 1.79 | 166.18 | 8.56 | 2.15 |
| 613-70-7 | Guaiacyl acetate | 1.55 | 166.18 | 8.18 | 1.57 |
| 616-44-4 | 3-Methylthiophene | 2.23 | 98.16 | 8.51 | 1.52 |
| 6191-71-5 | cis-4-Hepten-1-ol | 1.77 | 114.19 | 8.46 | 2.11 |

-continued

| CAS Number | Name | LogP (v3.0) | Formula Weight | Odor Detection Threshold, Neural Net model | bCD Complex Stability Constant |
|---|---|---|---|---|---|
| 6192-44-5 | beta-Phenoxy ethyl acetate | 1.87 | 180.20 | 8.51 | 1.26 |
| 61931-81-5 | cis-3-Hexenyl lactate | 1.34 | 172.22 | 8.20 | 1.76 |
| 620-23-5 | meta-tolyl aldehyde | 2.13 | 120.15 | 8.79 | 2.38 |
| 623-15-4 | 4-(2-Furyl)-3-buten-2-one | 1.7 | 136.15 | 8.42 | 1.38 |
| 624-92-0 | Dimethyl disulfide | 1.06 | 94.19 | 8.64 | 0.27 |
| 6290-14-8 | Cyclopentyl isobutyrate | 2.29 | 156.22 | 8.42 | 2.08 |
| 6314-97-2 | Phenylacetaldehyde diethyl acetal | 2.29 | 194.27 | 9.02 | 2.37 |
| 637-65-0 | tetrahydrofurfuryl propionate | 0.93 | 158.20 | 8.02 | 2.07 |
| 638-02-8 | 2,5-Dimethylthiophene | 2.36 | 112.19 | 8.64 | 2.04 |
| 64988-06-3 | Ethyl 2-methoxybenzyl ether | 1.98 | 166.22 | 8.23 | 2.27 |
| 65405-67-6 | p-Methoxy-alpha-methyl cinnamaldehyde | 2 | 176.22 | 8.85 | 1.16 |
| 65405-73-4 | Geranyl oxyacetaldehyde | 2.32 | 196.29 | 8.71 | −1.88 |
| 67028-40-4 | Ethyl (p-tolyloxy)acetate | 2.49 | 194.23 | 8.45 | 2.18 |
| 6728-26-3 | Trans-2-Hexenal | 1.57 | 98.14 | 8.41 | 2.26 |
| 6728-31-0 | cis-4-Heptenal | 1.85 | 112.17 | 9.51 | 2.33 |
| 67633-97-0 | 3-Mercapto-2-pentanone | 1.37 | 118.19 | 8.86 | 0.23 |
| 67634-07-5 | 3,5,6-Trimethyl-3-cyclohexene-1-carbaldehyde | 2.37 | 152.24 | 8.63 | 1.97 |
| 67634-16-6 | Floralol | 1.83 | 140.23 | 8.38 | 1.50 |
| 67634-17-7 | 2,4-Dimethyl-3-cyclohexene-1-methanol | 1.81 | 140.23 | 8.51 | 1.61 |
| 67746-30-9 | trans-2-Hexenal diethyl acetal | 2.34 | 172.27 | 8.19 | 2.13 |
| 67801-65-4 | 3,6-ivy carbaldehyde | 1.8 | 138.21 | 9.25 | 2.09 |
| 67845-46-9 | p-Methyl phenoxy acetaldehyde | 1.76 | 150.18 | 8.64 | 2.40 |
| 6789-80-6 | (Z)-3-hexen-1-al | 1.43 | 98.14 | 8.97 | 2.26 |
| 68039-48-5 | Dimethyl cyclohexene carboxaldehyde | 1.82 | 138.21 | 9.18 | 1.65 |
| 68039-49-6 | 2,4-Dimethyl-3-Cyclohexene-1-carboxaldehyde (Ligustral) | 1.78 | 138.21 | 9.24 | 1.76 |
| 68133-76-6 | cis-3-Hexenyl pyruvate | 1.9 | 170.21 | 8.50 | 1.30 |
| 68737-61-1 | 3,5-ivy carbaldehyde | 1.82 | 138.21 | 9.18 | 1.65 |
| 698-76-0 | delta-Octalactone | 2.03 | 142.20 | 8.24 | 2.83 |
| 699-10-5 | Methyl benzyl disulfide | 2.47 | 170.29 | 8.45 | 2.96 |
| 701-70-2 | 1-Phenylbutan-2-ol | 2.21 | 150.22 | 8.59 | 2.26 |
| 7452-79-1 | Ethyl 2-methylbutyrate | 1.91 | 130.19 | 7.27 | 1.75 |
| 74-93-1 | Methyl mercaptan | 0.58 | 48.10 | 8.63 | 0.43 |
| 7493-63-2 | Allyl anthranilate | 2.31 | 177.20 | 8.48 | 1.95 |
| 7493-71-2 | Allyl tiglate | 1.86 | 140.18 | 8.12 | 0.69 |
| 75-08-1 | Ethanethiol | 1.37 | 62.13 | 8.87 | 0.63 |
| 75-18-3 | dimethyl sulfide | 1.24 | 62.13 | 8.33 | 0.86 |
| 75-33-2 | 2-Propanethiol | 1.65 | 76.16 | 9.26 | 0.87 |
| 7540-51-4 | (−)-Citronellol | 2.49 | 156.27 | 8.37 | 0.64 |
| 7549-33-9 | Anisyl propionate | 2.23 | 194.23 | 8.45 | 2.08 |
| 75-66-1 | tert-Butyl mercaptan | 1.65 | 90.18 | 9.13 | 1.13 |
| 764-40-9 | 2,4-Pentadienal | 0.7 | 82.10 | 8.16 | 2.37 |
| 76649-25-7 | 3,6-Nonadien-1-ol | 2.45 | 140.23 | 9.52 | 2.16 |
| 774-48-1 | Benzaldehyde diethyl acetal | 2.03 | 180.25 | 8.57 | 2.35 |
| 7774-74-5 | 2-Thienyl mercaptan | 1.77 | 116.20 | 8.00 | 0.81 |
| 7774-79-0 | 4-(p-Tolyl)-2-butanone | 2.46 | 162.23 | 8.64 | 2.01 |
| 7774-96-1 | Isoeugenyl formate | 2.35 | 192.21 | 8.84 | 2.71 |
| 7786-44-9 | 2,6-Nonadien-1-ol | 2.43 | 140.23 | 9.59 | 2.24 |
| 7786-61-0 | 2-Methoxy-4-vinylphenol | 2.24 | 150.18 | 8.71 | 2.37 |
| 7786-67-6 | p-Menth-8-en-3-ol (8CI) | 2.48 | 154.25 | 8.42 | 2.29 |
| 81925-81-7 | filbert heptenone (Filbertone) | 2.31 | 126.20 | 8.06 | 1.92 |
| 84434-18-4 | Gardamide | 2.16 | 191.27 | 8.08 | 1.98 |
| 85-91-6 | Dimethyl anthranilate | 2.19 | 165.19 | 8.13 | 2.08 |
| 870-23-5 | Allyl mercaptan | 1.42 | 74.14 | 9.00 | 0.85 |
| 87-25-2 | Ethyl anthranilate | 2.05 | 165.19 | 8.58 | 1.84 |
| 874-66-8 | cinnamon acrolein | 1.29 | 136.15 | 8.09 | 0.92 |
| 881-68-5 | Vanillin acetate | 0.95 | 194.19 | 8.11 | 1.94 |
| 89-79-2 | Isopulegol | 2.48 | 154.25 | 8.42 | 2.29 |
| 90-02-8 | Salicylaldehyde | 1.4 | 122.12 | 8.95 | 2.21 |
| 90-05-1 | Guaiacol | 1.33 | 124.14 | 8.06 | 1.98 |
| 90-87-9 | Hydratropaldehyde dimethyl acetal | 2.12 | 180.25 | 8.60 | 2.24 |
| 91-64-5 | Coumarin | 1.68 | 146.15 | 8.55 | 2.47 |
| 928-94-9 | (Z)-2-hexen-1-ol | 1.3 | 100.16 | 8.09 | 2.06 |
| 928-95-0 | (E)-2-hexen-1-ol | 1.3 | 100.16 | 8.09 | 2.06 |
| 928-96-1 | cis-3-Hexen-1-ol | 1.3 | 100.16 | 8.06 | 2.06 |
| 93-16-3 | Methyl isoeugenol | 2.05 | 178.23 | 8.70 | 2.49 |
| 93-29-8 | Isoeugenyl acetate | 2.17 | 206.24 | 8.38 | 1.94 |
| 93-53-8 | 2-phenyl propionaldehyde | 2.06 | 134.18 | 8.43 | 2.21 |
| 93-54-9 | 1-Phenyl-1-propanol | 1.77 | 136.19 | 8.21 | 2.03 |

-continued

| CAS Number | Name | LogP (v3.0) | Formula Weight | Odor Detection Threshold, Neural Net model | bCD Complex Stability Constant |
|---|---|---|---|---|---|
| 93-58-3 | Methyl benzoate | 1.86 | 136.15 | 8.03 | 2.00 |
| 93-89-0 | Ethyl benzoate | 2.25 | 150.18 | 8.60 | 2.18 |
| 93893-89-1 | Citronitrile | 2.34 | 171.24 | 8.57 | 1.27 |
| 93-92-5 | Styrallyl acetate | 2.2 | 164.20 | 8.18 | 1.54 |
| 94089-01-7 | Butanoic acid, 2-methyl-, 2-hexenyl ester, (E)- | 1.6 | 134.24 | 9.32 | 1.41 |
| 94-86-0 | Vanitrope | 2.42 | 178.23 | 8.53 | 2.39 |
| 95-20-5 | 2-Methylindole | 2.43 | 131.18 | 8.53 | 2.58 |
| 97-53-0 | Eugenol | 2.21 | 164.20 | 8.57 | 2.51 |

One grouping of perfume raw materials that have a cyclodextrin binding coefficient of about 3.0 or less, a cLogP of about 2.5 or less, and a weight average molecular weight of about 200 Daltons or less includes beta gamma hexanol; cis 3 hexenyl acetate; ethyl-2-methyl butyrate; amyl-acetate (isomer blends); vanillin; anethole; methyl isoeugenol; guiacol; floralol; ethyl vanillin; 2,6-nonadien-1-ol; coumarin; and combinations thereof.

Another group of perfume raw materials that have a cyclodextrin binding coefficient of about 3.0 or less, a ClogP of about 2.5 or less, and a weight average molecular weight of about 200 Daltons or less includes ethyl-2-methyl butyrate; beta gamma hexanol; iso amyl acetate; amyl acetate; cis-3-Hexenyl acetate; gamma-Octalactone; ethyl vanillin; vanillin; benzaldehyde; and combinations thereof.

An additional group of perfume raw materials that have a cyclodextrin binding coefficient of about 3.0 or less, a ClogP of about 2.5 or less, and a weight average molecular weight of about 200 Daltons or less includes dimethyl anthranilate; iso-eugenyl acetate; canthoxal; 3,6-nonadien-1-ol, triplal; and combinations thereof.

Some examples of perfume raw materials with an odor detection threshold of 7–log ppb or more include can be found in the chart above.

In certain embodiments, the present invention relates absorbent articles that include perfumes in the form of a liquid. Therefore, it goes without saying that the perfumes of the present invention encompass any composition comprising any of the ingredients cited herein, in any embodiment wherein each such ingredient is independently present in any appropriate amount as defined herein. Many such compositions, over and above that which is specifically set out herein, can be encompassed.

The perfume of the absorbent article of the present invention may be applied on any of the layers making up the absorbent article, for example in liquid form using a liquid or spray applicator. The composition can also be applied in any other form which is known in the art for applying conventional perfumes to absorbent articles.

The perfume can be applied in a variety of ways, and in a variety of patterns, to the absorbent article. For example, the perfume can be applied in droplets or spray, or using conventional glue or liquid application equipment such as a slot applicator, which can be used for striped patterns, or air assisted applicators for patterned applications (like spray, spiral, serpentine, fibrils, Omega®, Signature® and the like) because this allows one to position the perfume in a preferred way (i.e., in a feminine care article the material might not be applied in correspondence with the vaginal opening if so desired). Also, patterned applications are helpful because they allow a precise application so that it is easier to avoid contact with the glue which connects the various layers of the absorbent article and which can interact with perfume ingredients.

The perfume can also be incorporated into a liquid or semi-solid carrier and applied as a lotion. The carrier can be polysiloxane oil, mineral oil, petrolatum, polyethylene glycol, glycerin, PEG, PPG and the like, and mixtures thereof.

The perfume of the present invention can also be introduced in the absorbent articles as complexed or encapsulated materials, e.g., capsules containing the perfume can be introduced into the absorbent article in such a way that these capsules are broken or dissolved and their content is released when the absorbent article is used or comes into contact with a malodorous liquid.

The perfume is typically disposed in the absorbent article in an amount of from about 0.01 to about 1000 milligrams per absorbent article, in some embodiments from about 0.1 to about 100 milligrams per absorbent article, or from about 0.1 to about 500 milligrams per absorbent article.

An effective amount of the perfume, typically from about 1 µL to about 10,000 µL, preferably from about 10 µL to about 1,000 µL, more preferably from about 25 µL to about 500 µL, or most preferably from about 50 µL to about 100 µL, or combinations thereof, is applied to the suitable substrate. Alternatively, an effective amount of the perfume of the present invention is from about 1 µL, 10 µL, 25 µL or 50 µL to about 100 µL, 500 µL, 1,000 µL or 10,000 µL. The perfume may be applied by hand to the absorbent article or applied utilizing a delivery apparatus such as a sprayer. Preferably, the perfume is allowed to dry after its application to the substrate.

In combination with the described perfumes, the absorbent articles of the invention may also comprise odor controlling materials as known in the art. For example, the absorbent articles may comprise odor absorbers such as silica, zeolites, active carbon and the like. Alternatively or in combination, the absorbent articles may also comprise reactive odor control materials such as those described in EP1842564 and EP2512526. Reactive compounds can also be introduced into the absorbent articles as liquids, but preferably, due to their reactivity, as encapsulated materials as described in WO2014205047, or complexes such as cyclodextrin complexes as known in the art and described for example in EP2114331.

Absorbent Articles

Most absorbent hygienic articles of the present invention (except those for internal use such as tampons) typically comprise a topsheet, a backsheet, and an absorbent core disposed between the topsheet and backsheet.

The topsheet of the absorbent hygienic article is preferably compliant, soft feeling, and non-irritating to the wearers skin and hair. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers), polymeric materials such as apertured formed thermoplastic films, apertured plastic films, and hydroformed thermoplastic films, porous foams, reticulated foams, reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

The backsheet can be impervious to liquids (e.g., menses and/or urine) and can be preferably manufactured from a thin plastic film, although other flexible materials may also be used such as nonwovens. As used herein, the term "flexible" refers to materials which are compliant and will readily conform to the general shape and contours of the human body. The backsheet can prevent the exudates absorbed and contained in the absorbent core from wetting articles which contact the absorbent article such as bedsheets, pants, pajamas and undergarments. The backsheet can also be vapor permeable ("breathable"), while remaining fluid impermeable. The backsheet may comprise a woven or nonwoven material, polymeric films such as thermoplastic films of polyethylene or polypropylene, or composite materials such as a film-coated nonwoven material.

The backsheet can comprise panty fastening means applied on its surface, particularly the surface facing outside the absorbent article in order to allow the article to stay in place when worn between the user's crotch and panties. Such panty fastening means can be for example a layer of adhesive or mechanical means such as Velcro® or combinations thereof. When an adhesive is present, typically a release paper is also present in order to protect the adhesive before use.

The backsheet and the topsheet can be positioned respectively adjacent the garment surface and the body surface of the absorbent core. The absorbent core can be joined with the topsheet, the backsheet, or both in any manner as is known by attachment means such as those well known in the art. Embodiments of the present invention are envisioned wherein portions of the entire absorbent core are unattached to either the topsheet, the backsheet, or both.

The absorbent core can be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers. Other suitable absorbent core materials include absorbent foams such as polyurethane foams or high internal phase emulsion ("HIPE") foams. Suitable HIPE foams are disclosed in U.S. Pat. No. 5,550,167, U.S. Pat. No. 5,387,207, U.S. Pat. No. 5,352,711, and U.S. Pat. No. 5,331,015.

For some absorbent articles, the absorbent core can be relatively thin, less than about 5 mm in thickness, or less than about 3 mm, or less than about 1 mm in thickness. Thickness can be determined by measuring the thickness at the midpoint along the longitudinal centerline of the pad by any means known in the art while under a uniform pressure of 1.72 kPa.

The absorbent core can comprise superabsorbent materials such as absorbent gelling materials (AGM), including AGM fibers, as is known in the art. The absorbent core can therefore constitute a layer comprising superabsorbent material.

The absorbent article can comprise other additional components, for example between the topsheet and absorbent core, such as a secondary topsheet or acquisition layer. The secondary topsheet or acquisition layer can comprise a tissue layer or a nonwoven, such as carded resin-bonded nonwovens, embossed carded resin-bonded nonwovens, high-loft carded resin-bonded nonwovens, carded through-air-bonded nonwovens, carded thermo-bonded nonwovens, spunbonded nonwovens, and the like. A variety of fibers can be used in the secondary topsheet or acquisition layer, including natural fibers, e.g. wood pulp, cotton, wool, and the like, as well as biodegradable fibers, such as polylactic acid fibers, and synthetic fibers such as polyolefins (e.g., polyethylene and polypropylene), polyesters, polyamides, synthetic cellulosics (e.g., RAYON®, Lyocell), cellulose acetate, bicomponent fibers, and blends thereof. The basis weight of the secondary topsheet or acquisition layer can vary depending upon the desired application.

The absorbent article can comprise further components such as side cuffs, typically found in diapers, or side wings or side flaps, typically found in sanitary napkins.

Absorbent catamenial tampons are absorbent articles for internal use in the vagina which are typically made by a pledget comprising absorbent fibers compressed to a cylindrical shape. Tampons can be "digital tampons" when they have a self-sustaining shape and can be inserted with a finger or "applicator tampons" i.e., tampons which are introduced using an applicator. Tampons can also comprise an extraction cord to facilitate extraction from the vagina. Pessaries may also be used as absorbent articles to manage adult incontinence in female consumers. Their construction may be similar to tampons but may also take different shapes.

The absorbent hygienic articles herein are preferably disposable after a single use.

Absorbent hygienic articles herein are often commercialized in packages containing a plurality of units, often the package is a plastic film or a carton box. Single units contained within the commercial package can be individually packaged or not.

Cyclodextrin Complex Positioning

The cyclodextrin complex of the present invention can be disposed in various locations in or on the absorbent article. In all cases, the cyclodextrin complex can be simply applied on a surface of the article using any application method. More specifically in the case of paper towels, wipes, toilet paper and facial tissues the cyclodextrin complex can be applied on any surface of any of the layers making up the article or be mixed with the fibers during the making process.

In the case of absorbent hygienic articles, the cyclodextrin complex can be disposed on the garment-facing side or the body-facing side of the topsheet or absorbent core, or on the body-facing side of the backsheet. Preferably, the cyclodextrin complex is disposed on the absorbent core, and preferably on the body-facing side of the absorbent core. The cyclodextrin complex can also be disposed on other components of the absorbent article, when present, such as the garment-facing side or body-facing side of a secondary topsheet or acquisition layer. The cyclodextrin complex can also be mixed with any of the fibers or materials making up any of the layers of the absorbent article.

In certain embodiments, the cyclodextrin complex of the present invention is disposed in the absorbent article in or on a layer that is closer to the body-facing surface of the absorbent article than the absorbent core or a layer comprising superabsorbent material (e.g. absorbent gelling material ("AGM")). In general, for the cyclodextrin complex to effectively release the compound it needs to come in contact with moisture. A problem exists when incorporating a cyclodextrin complex in an absorbent hygienic article, because other components, such as the absorbent core and/or superabsorbent material, of the absorbent article have a strong affinity for bodily fluids. When an absorbent article is insulted with bodily fluid, such as menses or urine, the cyclodextrin complex is in competition with the absorbent core and/or superabsorbent material for the moisture contained in the bodily fluid. The absorbent core and/or superabsorbent material has a strong affinity for the moisture and once the absorbent core and/or superabsorbent material contacts the bodily fluid, the absorbent core and/or superabsorbent material effectively "lock-up" the moisture of the bodily fluid, thereby reducing the amount of moisture available to contact the cyclodextrin complex and release the compound to provide odor control benefits. Surprisingly, it has been discovered that if the cyclodextrin complex is coated onto the outside surface of the AGM particle, that this can actually speed activation and release of the cyclodextrin and fragrance complex. Without being bound by theory it is believed that the high solubility of the complexes of the present invention and the relatively slow kinetic of absorption by the AGM particles allow the complete dissolution of the complexes before the AGM granule is able to compete for the liquid absorption and the location of the cyclodextrin complex on the surface of the AGM granule provides for a complete release exactly when and there it may be needed, i.e., where a possible malodorant liquid is present. This results in more effective release of the complexed odor controlling organic compounds and provides improved odor control benefits.

In the case of catamenial tampons, the cyclodextrin complex can be present on or in any component of the tampon, including the absorbent compressed pledget forming the tampon body, the overwrap, and the extraction cord. For example, it can be comprised in the tampon body, or on the tampon surface or, if an overwrap is present, on either surface of the overwrap. In case a secondary mass of absorbent material is present along the extension cord proximal to the extraction end of the tampon, the cyclodextrin complex can be comprised within this secondary mass.

In all cases the cyclodextrin complex of the invention can be applied on one of the layers making up the absorbent article in powder form or can be incorporated into a liquid or semi-solid carrier and applied as a lotion. In this case the cyclodextrin complexes can be dispersed in a carrier to form a dispersion, and the dispersion applied to the absorbent article. The carrier can be selected for example from the group consisting of polysiloxane oil, mineral oil, petrolatum, polyethylene glycol, glycerin and the like, and mixtures thereof. The carrier is preferably polysiloxane oil, such as a silicone glycol copolymer (commercially available from Dow Corning as Dow Corning 190 Fluid). The dispersion can be applied using conventional glue application equipment such as a slot applicator, which can be used for striped patterns, or air assisted applicators for patterned applications (like spray, spiral, serpentine, fibrils, Omega®, Signature® and the like). Patterned applications are in this case preferred because this allows one to position the complex in a way that it does not impact fluid acquisition (i.e., in a fem care article the material could not be applied in correspondence with the vaginal opening) and the pattern, having a large void space, allows fluid penetration also on the sides. Also, patterned applications are helpful because they allow a precise application so that it is easier to avoid contact with the glue which connects the various layers of the absorbent article.

A preferred method for applying the cyclodextrin complex of the invention into the absorbent article, however, is to form the complex directly in the site of the application. This is made possible by the fact that substituted cyclodextrins according to the invention have an improved solubility both in water and in ethanol based solvents. This improved solubility allows one to prepare cyclodextrin complexes in the site of application (e.g., on a layer of material which is part of an absorbent article) using an alternative method which is not applicable with unsubstituted cyclodextrins which have lower solubility. In this method, the substituted cyclodextrin is solubilized in a solvent system which comprises at least 60% preferably at least 80% more preferably at least 95% of volatile solvents e.g. water, C1-C8 alcohols, C1-C8 ketone and aldehydes, C1-C8 hydrocarbons, supercritical fluids, or even cooled gases in fluid form such as liquid nitrogen ethanol or mixtures thereof, together with the odor controlling organic compound forming a solution.

The solvent system preferably comprises less than 5%, preferably less than 1.0%, and more preferably less 0.5% of any non-volatile solvent(s) having a C Log P value less than 3 because they can interfere negatively with the crystallization of the CD complex.

Preferably, the viscosity of the solution is such that is easily pumpable or sprayable (if desired). This viscosity is preferably less than 60 cp at 20° C., more preferably less than 40 cp at 20° C. (Brooksfield viscosity, measured at 20 $sec^{-1}$ and spindle 40 mm SST HB ST). Viscosity can be lowered by further diluting the solution. If solutions are prepared ahead of time (prior to use), and water is used in combination with ethanol, then the ratio of water to ethanol should be chosen to prevent the formation of microbial growth in storage. Preferably the ratio of ethanol to water is at least 4/6 by weight. Preferably, the odor controlling organic compound and the substituted cyclodextrin are added to this mixture at a molar ratio of between 0.25:1 to 4:1. More preferably, this ratio is between 0.5:1 to 2:1. Most preferably, this ratio is between 0.8:1 to 1.2:1. The resulting solution can be applied on any substrate making up the absorbent article with any type of applicator for liquid compositions e.g. with a drop applicator or a spray applicator. After application, upon evaporation of the volatile solvent, the complex is surprisingly formed in situ without the need of additional carriers for the application, and the degree of complexing achieved is high.

It is believed that when the solvent which dissolves the cyclodextrin derivative evaporates, the cyclodextrin derivative can crystallize into a number of small microcrystals featuring different crystal shapes which therefore do not stack thus allowing fluid to better penetrate and activate them when in use. Being formed in the presence of a fibrous substrate the crystals tend to entrap some fibers and therefore to bind to it. This binding is advantageous because not only loss of the odor controlling organic compound is prevented but also positioning and dosing is facilitated as the complex forms and remains in the place where the solution is applied.

Naturally, it is important that during the manufacturing process the volatile solvent evaporates as much as possible before the products are sealed into air tight plastic bags as it common for absorbent articles. Articles can be heated during manufacturing in order to facilitate the evaporation of the solvent, but this may not be necessary.

When the cyclodextrin complex is introduced into the absorbent article as a coating on AGM particles, the coating can be obtained by depositing and evaporating a solution comprising the cyclodextrin and the one or more odor controlling organic compound as described above in the case of the application to any other layer or material of the absorbent article. Also, any other known coating method can be used.

More precisely coated AGM granules can be obtained, directly during the manufacturing operation of the absorbent article by spraying or otherwise depositing a solution comprising the cyclodextrin and the one or more odor controlling organic compounds dissolved in appropriate solvents as described above (e.g., ethanol, water, and mixtures thereof) onto the surface of the AGM in the assembly line. This deposition may occur before or after its application within the absorbent article (i.e., AGM can be treated with the cyclodextrin complex solution when still in the drum, before application to the absorbent article or after having been deposited onto the absorbent article.

Alternatively, pre-coated AGM granules can be prepared in advance, e.g., by the AGM supplier and directly dosed in the manufacturing of the absorbent article, with the additional advantage of not having to control the evaporation of the solvent during the manufacturing of the article, especially in cases where the article is manufactured at high speeds and then packaged in air tight packages.

Any suitable method of coating or application to the outside surface is appropriate. One method is to spray or mist a solution of the dissolved cyclodextrin, odor controlling organic compound(s) and appropriate solvents as described above onto the dry AGM particle surface (in this case it may be advantageous if the moisture of the dry AGM particle is less than about 20% moisture, preferably less than 10% moisture). Another method is to coat the AGM particle using the same solution and equipment such as a Wurster spray coater, commonly used to apply coatings to the outside surface of particles. Another method is to spray a solution on to a moving bed of dry AGM particles using a mist or spray applicator capable of creating a droplet size less than about half the size of AGM particle. Alternatively, effective coating of AGM particles can also be obtained by rapidly dipping a bed of AGM particles into a tank of a solution of the dissolved cyclodextrin, odor controlling organic compound(s) and appropriate solvents as described above, and remove it immediately thereafter to coat the outside surface without swelling the AGM particle. In all cases, an appropriate drying step should follow using techniques which are common in the art. This said, forming coating on solid particles is a known process so that a skilled person would have many methods available in the common knowledge to achieve effective coating of the particles, as long as a method does not require the AGM particles to be in prolonged contact with a large amount of water or other fluids which would swell the particle, that coating method would be suitable for obtained coated AGM particles according to the invention.

Generally, it is preferred to apply a coating that results in a perfume: AGM weight ratio of between 1:100,000 to 1:1000.

In absorbent articles of the present invention that are useful for personal hygiene, the typical amounts may vary based on the specific application of the article. Table III indicates the following range amounts that are suitable. The weight indicated below only refers to the one or more perfumes and not to the cyclodextrin complex. In most cases, a 1:1 molecular weight ratio of the perfume(s) to the cyclodextrin is targeted.

TABLE III

Perfume Amounts Typical in Products

| Absorbent Article | Range (mg) | |
|---|---|---|
| | Min | Max |
| Panty Liners | 0.1 | 5 |
| Sanitary Napkins | 0.2 | 20 |
| Adult Incontinence Pads | 0.5 | 30 |
| Adult Incontinence Diapers | 1 | 50 |
| Baby Diapers and Pants | 1 | 50 |

The present invention further encompasses a method of reducing malodor associated with malodorous fluids, e.g., bodily fluid such as urine, menses, and/or feces, comprising the step of contacting the fluid with an absorbent article of the present invention. Preferably, the method reduces the malodor associated with the malodorous fluids.

The present invention also encompasses a method of making an absorbent article which comprises the step of applying onto one of the materials making up the article the cyclodextrin complexes according to the present invention. The material of the article may be selected from the group of the topsheet, backsheet, core, and combinations thereof.

In Vitro Perfume Release Method

Released Perfume (RP) Sample

About 500 milligrams of a cyclodextrin complex is weighed into a glass scintillation vial. About 1 milliliter of water is added to the vial. The vial is then capped tightly and vortexed for about 30 seconds to create a slurry. The RP sample is then placed into a 37 degrees Celsius oven to incubate for 4 hours. The sample vial is removed from the oven and allowed to cool to room temperature. 10 milliliters of hexane is then added to the vial. The vial is capped tightly and mixed by hand shaking for about 10 seconds and then mixed on high speed with a vortex mixer for about 30 seconds to extract perfume components liberated by the water incubation step. After allowing solids to settle, an aliquot of the sample is transferred to a 2 milliliter autosampler vial for analysis. Total Perfume (TP) Sample Another 500 milligrams of the same cyclodextrin complex used to create the RP sample is weighed into a scintillation vial. About 10 milliliters of acetone is added to the vial. This sample is then capped tightly and vortexed for about 30 seconds to disperse the sample. The total sample is then placed into a 70 degrees Celsius oven for 4 hours. The sample is removed from the oven and allowed to cool to room temperature. After allowing solids to settle, an aliquot of the sample is transferred to a 2 milliliter autosampler vial for analysis.

Analysis

The RP and TP samples are analyzed using liquid injection gas chromatography with a mass selective detector. The injection port is heated to 270 degrees Celsius and operated in split mode with a split ratio of about 20:1. The carrier gas is helium and delivered at a constant flowrate of about 1.2 milliliters per minute. The oven temperature is ramped from an initial temperature of 50 degrees Celsius to a final temperature of 250 degrees Celsius at a rate of 10 degrees Celsius per minute. The final temperature is held for 2 minutes. The mass selective detector is operated in scanning mode and perfume components are identified using NIST mass spectral library searching. The chromatogram from the TP sample is used to identify a specific mass to charge ratio for each perfume component and extracted ion peak areas for each perfume component are obtained. The RP chromatogram is correspondingly processed.

Results Calculation

Individual perfume component peak areas per unit of sample weight from the RP sample are divided by the corresponding peak areas per unit of sample weight from the TP sample. The resulting ratio is multiplied by 100 to calculate a release percentage for each individual perfume material. The release percentages from all perfume components are averaged to calculate a composite release value for a given complex sample.

Perfume raw materials suitable for inclusion into a perfume for the absorbent articles of the invention can include:

| Material | % by weight of perfume |
|---|---|
| Cis-3-hexen-1-ol | 5-50% |
| Cis-3-hexenyl acetate | 5-50% |
| Ethyl 2-methylbutyrate | 5-50% |
| Isoamyl acetate | 5-50% |
| Vanillin | 5-50% |

Additional information about the perfume raw materials in the exemplary perfumes can be found in the table below:

| CAS Number | Name | cLogP | Weight average molecular weight (Dalton) | Odor Detection threshold (-log molar concentration) | Cyclodextrin stability constant (log K) |
|---|---|---|---|---|---|
| 123-92-2 | Isoamyl acetate | 1.87 | 130 | 7.12 | 0.33 |
| 121-33-5 | Vanillin | 1.04 | 152 | 9.93 | 1.36 |
| 7452-79-1 | Ethyl 2-methylbutyrate | 1.91 | 130 | 7.27 | 0.75 |
| 928-96-1 | Cis-3-hexen-1-ol | 1.3 | 100 | 8.06 | 1.06 |
| 3681-71-8 | Cis-3-hexenyl acetate | 2.18 | 142 | 8.16 | 0.48 |

These resultant perfumes can be made by blending all of the perfume raw materials together until a homogenous solution is formed.

These perfumes can then be formed into a cyclodextrin complex by mixing 10 parts cyclodextrin with 10 (or more) parts water, and 1 part (or less) of a perfume constituting the PRMs listed above in varying amounts. After the mixing, the slurry will be more viscous than at the start of mixing—the change in viscosity is believed to be due to the formation of the cyclodextrin complex. The mixture is then dried (or spray dried) to remove the water and leave the cyclodextrin complex as a powder.

This powder can be used in powder or liquid form. In the examples below, the perfumes are used at a level of from about 0.00001 mg to about 50 mg by combining a perfume at a level of about 0.01% to about 30% based on total perfume weight. Examples of various absorbent articles are as follows:

Example A: Sanitary Napkins or Pads for Menstrual Odor Control

The cyclodextrin complexes above are used on a sanitary napkin or pad. A cyclodextrin complex samples in the amount of 1 mg, 5 mg, 10 mg, 15 mg, and 20 mg in powder form is prepared as described above by combining a larger batch 55 gms of distilled water, 41 gms of cyclodextrin, and 4 gms of an exemplary perfume which includes the suitable PRMs listed above. Once the complex is formed and dried the each of the samples is added onto a garment facing side of a secondary topsheet of an Always Ultra Thin Unscented menstrual pad. This results in 5 separate pads. Optionally, a second cyclodextrin complex can be added to each of the pads in an amount that is different than the first cyclodextrin complex. This second cyclodextrin complex is preferably added beneath the core of the pad.

Example B: Adult Incontinence Pants for Urine Odor Control

The cyclodextrin complexes above are used separately as a perfume component on an AI pant product. A cyclodextrin complex sample is prepared as described above by combining 40 grams of the powdered complex with 60 gms of silicon glycol copolymer (Cow Corning 190 Fluid). A 20 mg, 30 mg, 40 mg, and 50 mg sample of the liquid cyclodextrin complex are each added onto a top surface of an Always Discreet Adult Incontinence Underwear, moderate absorbency on a garment-facing side of a secondary topsheet. This results in 4 AI pads. Optionally, a second cyclodextrin complex can be added to each pant product in an amount that is different than the first cyclodextrin complex. This second cyclodextrin complex is preferably added beneath the core of the article.

Example C: Diapers for Odor Control

The cyclodextrin complexes above are used separately as a perfume component on a Pampers Cruisers Baby Diaper (size 4). A cyclodextrin complex sample in powder form (as mentioned relative to Example A) in an amount of 10 mg, 20 mg, 30 mg, 40 mg, and 50 mg is added onto a Pampers Cruisers Baby Diaper on the garment-facing surface of a secondary topsheet. This results in 5 diapers. Optionally, a second cyclodextrin complex that is different from the first cyclodextrin complex can be added. This second cyclodextrin complex is preferably added beneath the core of the diaper.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a perfume comprising perfume raw materials, wherein 40% or more, by weight of the perfume, of the perfume raw materials have:
   a) a cyclodextrin complex stability constant (log k) of less than about 3.0,
   b) a ClogP of about 2.5 or less; and
   c) a weight average molecular weight of about 200 Daltons or less.

2. The absorbent article of claim 1, wherein the cyclodextrin complex stability constant (log k) is from about −2.0 to about 2.5.

3. The absorbent article of claim 1, wherein the perfume raw materials are selected from the group consisting of eugenyl formate, benzaldehyde, 2-hexen-1-yl acetate, alpha-methyl cinnamaldehyde, methyl phenylacetate, viridine, ethyl 2-phenylacetate, methyl hydrocinnamate, methyl cinnamate, 2-Phenylethyl acetate, cinnamyl acetate, lilac acetaldehyde, 4-(p-Methoxyphenyl)-2-butanone, anethole, gamma-Octalactone, 3-phenyl propionaldehyde, cinnamic alcohol, cinnamic aldehyde, phenethyl formate, 3-phenyl propyl formate, isobutyl furylpropionate, styryl acetate, geranyl formate, 3-Hepten-1-ol, citronellol, trans-Geraniol, nerol, neral, melon heptenal, propyl mercaptan, 2-Propionylpyrrole, 5,6-Dimethyl-1-(1-methylethenyl)bicyclohept-5-ene-2-methanol, hydratopic alcohol, 3,4-Dimethoxyacetophenone, safranal, 2-Hydroxyacetophenone, cis-carveol, ocean propanal, Isosafrol, Indole, 2-Methylbenzothiazole, Ethyl vanillin, Vanillin, Methyl p-anisate, Benzyl propionate, 3-phenyl propyl acetate, phenyl acetaldehyde, p-Hydroxybenzaldehyde, para-anisaldehyde, Isoamyl acetate, Ethyl 3-methylthiopropionate, Methyl anthranilate, 1,2-Cyclopentanedione, 3-ethyl-, Syringaldehyde, furfuryl thioacetate, blackberry thiophenone, p-Cresyl acetate, linalool oxide (pyranoid), Geranial, Parmanyl, Sorbinaldehyde, Pentyl 2-furyl ketone, m-Guaiacol, alpha-Methylcinnamic alcohol, Ethyl cyclohex-3-enecarboxylate, 2,4-Hexadienyl acetate, 4-Hydroxy-3-methylbenzaldehyde, Furan, 3-methyl-2-(3-methyl-2-butenyl)-, n-Pentyl acetoacetate, Ethyl 2-hexenoate, 2-Ethyl-4-methylthiazole, tropical thiazole, Trifernal, Coumarone, 2,4-Hexadienyl propionate, Cyclopentyl mercaptan, 2-Methyl-2-butanethiol, trans-2-Methyl-2-pentenoic acid, 2-Hexyl-1,3-dioxolane, cis-3-Hepten-1-ol, 3-Hexenyl acetate, Trans,trans-2,4-Hexadien, methyl trans-cinnamate 99%, 4-Methyl-5-vinylthiazole, 2-Propylthiazole, (S),(−)-Perillaaldehyde, 2-(1-Methylpropyl)thiazole, (+)-p-menth-1-en-9-OL 97% (mixture of isomers), Isobutyl thiazole, trans-2-Heptenal, (1S)-(−)-cis-Verbenol, Anapear, alpha-Campholenic alcohol, Ethyl 2-mercaptopropionate, 2-Methylphenethyl alcohol, Methyl 4-phenylbutyrate, Allyl crotonate, Allyl butyrate, Benzyl lactate, Vanillin isobutyrate, perillaldehyde, Neryl Formate, Allyl methyl disulfide, Methyl propyl disulfide, 2-Cyclopenten-1-one, 2-hydroxy-3,4-dimethyl-, 3-Ethyl-2-hydroxy-2-cyclopenten-1-one, 2-Octenol-1, Tetrahydrofurfuryl butyrate, Allo-ocimenol, 7-Octene-1,6-diol, 3,7-dimethyl-, 3-Ethoxybenzaldehyde, 2-Ethylbenzaldehyde, 2-hexen-1-ol, Phenoxyethyl propionate, Nerolione, 7-Methylcoumarin, Butylacrolein, 2-Hexen-1-yl acetate, Ethyl phenoxyacetate, Ethyl trans-3-hexenoate, N-Acetyl methyl anthranilate, Ethyl trans-2-hexenoate, Vertoliff, (2E,6Z)-Nona-2,6-dien-1-ol, Ocimenol, 2,6-Dimethyl-1,5,7-octatrienol-3, p-Menth-1-ene-9-al, 2,4-Octadien-1-al, Propyl anthranilate, 2-Pentanoylfuran, 4-Ethyl-2-methylthiazole, Jasmolactone, cis-3-Hexenyl formate, 1-Octenol-3,4,5-Dimethylthiazole, 4,4-Dimethyl-5-isopropyl-1,3-dioxolane, 1-Hexen-3-yl acetate, Furfuryl valerate, 2,6-Dimethyl-6-hepten-1-ol, cis-3-Hexenyl acetate, trans-3-Hexenyl acetate, 5-Ethyl-2-thiophenecarbaldehyde, 2-Phenyl-1(2)propenyl-1 ester, 3-Cyclohexene-1-ethanol, 4-methyl-beta-methylene-, (R)-, Furfuryl hexanoate, 3-methoxy cinnamaldehyde, 3-Acetyl-5-butyldihydro-2(3H)-furanone, Pyrazine, 3-butyl-2,5-dimethyl-, Methyl Heptenone, 2,5-Dimethylthiazole, (E)-anethol, Phenylethyl oxy-acetaldehyde, 3-Ethyl-2-hydroxy-4-methylcyclopent-2-en-1-one, (E,E)-2,4-heptadien-1-al, Cinnamic aldehyde dimethyl acetal, Campholene aldehyde, cis-4-Hexenal, 2-Hepten-4-one, 2-Octen-4-one, Verbenol, 4-Ethylbenzaldehyde, Piperitol, piperitenone, Isocoumarin, Lepidine, ethyl maltol, Butyroin, Hinokitiol, Pyrazine, 2-butyl-3,5-dimethyl-, cis-3, cis-6-nonadienol, trans-2-Hexenyl formate, Ethyl 2-methyl-4-pentenoate, 1-(4-Methylphenyl)ethanol, Perillyl alcohol, Cumic alcohol, citral, Benzyl acetoacetate, p-Methylhydrocinnamic aldehyde, 2,4-Dimethylthiazole, Acetaldehyde phenyl ethyl acetal, Canthoxal, Ethyl 3-mercaptopropionate, Raspberry ketone, 2-Methylthiophene, 3,6-Octadienal, 3,7-dimethyl-, 2,4-Octadienal, Cinnamaldehyde ethylene glycol acetal, trans-3, cis-6-nonadienol, 2-Heptenal, (2Z)-, Methyl furfuryl disulfide, o-Acetylanisole, Lavandulol, 3-Methylacetophenone, p-Tolyl alcohol, Furfuryl thiopropionate, 2-Mercaptomethylpyrazine, 2,4-Heptadienal, cis-iso-Eugenol, S-Ethyl benzothioate, trans-Isoeugenol, Methyl 2-nitrobenzoate, Methyl o-methoxybenzoate, Guaiacyl acetate, 3-Methylthiophene, cis-4-Hepten-1-ol, beta-Phenoxy ethyl acetate, cis-3-Hexenyl lactate, meta-tolyl aldehyde, 4-(2-Furyl)-3-buten-2-one, Dimethyl disulfide, Cyclopentyl isobutyrate, Phenylacetaldehyde diethyl acetal, tetrahydrofurfuryl propionate, 2,5-Dimethylthiophene, Ethyl 2-methoxybenzyl ether, p-Methoxy-alpha-methyl cinnamaldehyde, Geranyl oxyacetaldehyde, Ethyl (p-tolyloxy)acetate, Trans-2-Hexenal, cis-4-Heptenal, 3-Mercapto-2-pentanone, 3,5,6-Trimethyl-3-cyclohexene-1-carbaldehyde, Floralol, 2,4-Dimethyl-3-cyclohexene-1-methanol, trans-2-Hexenal diethyl acetal, 3,6-ivy carbaldehyde, p-Methyl phenoxy acetaldehyde, (Z)-3-hexen-1-al, Dimethyl cyclohexene carboxaldehyde, 2,4-Dimethyl-3-Cyclohexene-1-carboxaldehyde, cis-3-Hexenyl pyruvate, 3,5-ivy carbaldehyde, delta-Octalactone, Methyl benzyl disulfide, 1-Phenylbutan-2-ol, Ethyl 2-methylbutyrate, Methyl mercaptan, Allyl anthranilate, Allyl tiglate, Ethanethiol, dimethyl sulfide 2-Propanethiol, (−)-Citronellol, Anisyl propionate, tert-Butyl mercaptan, 2,4-Pentadienal, 3,6-Nonadien-1-ol, Benzaldehyde diethyl acetal, 2-Thienyl mercaptan, 4-(p-Tolyl)-2-butanone, Isoeugenyl formate, 2,6-Nonadien-1-ol, 2-Methoxy-4-vinylphenol, p-Menth-8-en-3-ol, filbert heptenone, Gardamide, Dimethyl anthranilate, Allyl mercaptan, Ethyl anthranilate, cinnamon acrolein, Vanillin acetate, Isopulegol, Salicylaldehyde, Guaiacol, Hydratropaldehyde dimethyl acetal, Coumarin (Z)-2-hexen-1-ol, (E)-2-hexen-1-ol, cis-3-Hexen-1-ol, Methyl isoeugenol, Isoeugenyl acetate, 2-phenyl propionaldehyde, 1-Phenyl-1-propanol, Methyl benzoate, Ethyl benzoate, Citronitrile, Styrallyl acetate, Butanoic acid, 2-methyl-, 2-hexenyl ester, (E)-, Vanitrope, 2-Methylindole, Eugenol, and combinations thereof.

4. The absorbent article of claim 3, wherein the 40% or more of the perfume raw materials also have an Odor Detection Threshold of about 7 or more −log molar concentration.

5. The absorbent article of claim 3, wherein about 40% to about 100%, by weight of the perfume, of the perfume raw materials have a cyclodextrin binding coefficient of less than about 3.0, a ClogP of about 2.5 or less, and a weight average molecular weight of about 200 Daltons or less.

6. The absorbent article of claim 3, wherein the perfume raw materials have a weight average molecular weight of about 180 Daltons or less.

7. An absorbent article comprising a cyclodextrin complex which comprises a cyclodextrin and a perfume comprising perfume raw materials, wherein 40% or more, by weight of the perfume, of the perfume raw materials have: a cyclodextrin complex stability constant is about 3.0 or less, a ClogP of about 2.5 or less, and a weight average molecular weight of about 200 Daltons or less.

8. The absorbent article of claim 7, wherein the cyclodextrin complex stability constant (log k) is from about −2.0 to about 2.5.

9. The absorbent article of claim 7, wherein the cyclodextrin comprises an alpha-cyclodextrin, a beta-cyclodextrin, a gamma-cyclodextrin, or combinations thereof.

10. The absorbent article of claim 7, wherein the percent of the fragrance that is complexed with the cyclodextrin is greater than about 75%.

11. The absorbent article of claim 7, wherein the perfume raw materials are selected from the group consisting of: eugenyl formate, benzaldehyde, 2-hexen-1-yl acetate, alpha-methyl cinnamaldehyde, methyl phenylacetate, viridine, ethyl 2-phenylacetate, methyl hydrocinnamate, methyl cinnamate, 2-Phenylethyl acetate, cinnamyl acetate, lilac acetaldehyde, 4-(p-Methoxyphenyl)-2-butanone, anethole, gamma-Octalactone, 3-phenyl propionaldehyde, cinnamic alcohol, cinnamic aldehyde, phenethyl formate, 3-phenyl propyl formate, isobutyl furylpropionate, styryl acetate, geranyl formate, 3-Hepten-1-ol, citronellol, trans-Geraniol, nerol, neral, melon heptenal, propyl mercaptan, 2-Propionylpyrrole, 5,6-Dimethyl-1-(1-methylethenyl)bicyclohept-5-ene-2-methanol, hydratopic alcohol, 3,4-Dimethoxyacetophenone, safranal, 2-Hydroxyacetophenone, cis-carveol, ocean propanal, Isosafrol, Indole, 2-Methylbenzothiazole, Ethyl vanillin, Vanillin, Methyl p-anisate, Benzyl propionate, 3-phenyl propyl acetate, phenyl acetaldehyde, p-Hydroxybenzaldehyde, para-anisaldehyde, Isoamyl acetate, Ethyl 3-methylthiopropionate, Methyl anthranilate, 1,2-Cyclopentanedione, 3-ethyl-, Syringaldehyde, furfuryl thioacetate, blackberry thiophenone, p-Cresyl acetate, linalool oxide (pyranoid), Geranial, Parmanyl, Sorbinaldehyde, Pentyl 2-furyl ketone, m-Guaiacol, alpha-Methylcinnamic alcohol, Ethyl cyclohex-3-enecarboxylate, 2,4-Hexadienyl acetate, 4-Hydroxy-3-methylbenzaldehyde, Furan, 3-methyl-2-(3-methyl-2-butenyl)-, n-Pentyl acetoacetate, Ethyl 2-hexenoate, 2-Ethyl-4-methylthiazole, tropical thiazole, Trifernal, Coumarone, 2,4-Hexadienyl propionate, Cyclopentyl mercaptan, 2-Methyl-2-butanethiol, trans-2-Methyl-2-pentenoic acid, 2-Hexyl-1,3-dioxolane, cis-3-Hepten-1-ol, 3-Hexenyl acetate, Trans,trans-2,4-Hexadien, methyl trans-cinnamate 99%, 4-Methyl-5-vinylthiazole, 2-Propylthiazole, (S),(−)-Perillaaldehyde, 2-(1-Methylpropyl)thiazole, (+)-p-menth-1-en-9-OL 97% (mixture of isomers), Isobutyl thiazole, trans-2-Heptenal, (1S)-(−)-cis-Verbenol, Anapear, alpha-Campholenic alcohol, Ethyl 2-mercaptopropionate, 2-Methylphenethyl alcohol, Methyl 4-phenylbutyrate, Allyl crotonate, Allyl butyrate, Benzyl lactate, Vanillin isobutyrate, perillaldehyde, Neryl Formate, Allyl methyl disulfide, Methyl propyl disulfide, 2-Cyclopenten-1-one, 2-hydroxy-3,4-dimethyl-, 3-Ethyl-2-hydroxy-2-cyclopenten-1-one, 2-Octenol-1, Tetrahydrofurfuryl butyrate, Allo-ocimenol, 7-Octene-1,6-diol, 3,7-dimethyl-, 3-Ethoxybenzaldehyde, 2-Ethylbenzaldehyde, 2-hexen-1-ol, Phenoxyethyl propionate, Nerolione, 7-Methylcoumarin, Butylacrolein, 2-Hexen-1-yl acetate, Ethyl phenoxyacetate, Ethyl trans-3-hexenoate, N-Acetyl methyl anthranilate, Ethyl trans-2-hexenoate, Vertoliff, (2E,6Z)-Nona-2,6-dien-1-ol, Ocimenol, 2,6-Dimethyl-1,5,7-octatrienol-3, p-Menth-1-ene-9-al, 2,4-Octadien-1-al, Propyl anthranilate, 2-Pentanoylfuran, 4-Ethyl-2-methylthiazole, Jasmolactone, cis-3-Hexenyl formate, 1-Octenol-3, 4,5-Dimethylthiazole, 4,4-Dimethyl-5-isopropyl-1,3-dioxolane, 1-Hexen-3-yl acetate, Furfuryl valerate, 2,6-Dimethyl-6-hepten-1-ol, cis-3-Hexenyl acetate, trans-3-Hexenyl acetate, 5-Ethyl-2-thiophenecarbaldehyde, 2-Phenyl-1(2)propenyl-1 ester, 3-Cyclohexene-1-ethanol, 4-methyl-beta-methylene-, (R)-, Furfuryl hexanoate, 3-methoxy cinnamaldehyde, 3-Acetyl-5-butyldihydro-2(3H)-furanone, Pyrazine, 3-butyl-2,5-dimethyl-, Methyl Heptenone, 2,5-Dimethylthiazole, (E)-anethol, Phenylethyl oxy-acetaldehyde, 3-Ethyl-2-hydroxy-4-methylcyclopent-2-en-1-one, (E,E)-2,4-heptadien-1-al, Cinnamic aldehyde dimethyl acetal, Campholene aldehyde, cis-4-Hexenal, 2-Hepten-4-one, 2-Octen-4-one, Verbenol, 4-Ethylbenzaldehyde, Piperitol, piperitenone, Isocoumarin, Lepidine, ethyl maltol, Butyroin, Hinokitiol, Pyrazine, 2-butyl-3,5-dimethyl-, cis-3, cis-6-nonadienol, trans-2-Hexenyl formate, Ethyl 2-methyl-4-pentenoate, 1-(4-Methylphenyl)ethanol, Perillyl alcohol, Cumic alcohol, citral, Benzyl acetoacetate, p-Methylhydrocinnamic aldehyde, 2,4-Dimethylthiazole, Acetaldehyde phenyl ethyl acetal, Canthoxal, Ethyl 3-mercaptopropionate, Raspberry ketone, 2-Methylthiophene, 3,6-Octadienal, 3,7-dimethyl-, 2,4-Octadienal, Cinnamaldehyde ethylene glycol acetal, trans-3, cis-6-nonadienol, 2-Heptenal, (2Z)-, Methyl furfuryl disulfide, o-Acetylanisole, Lavandulol, 3-Methylacetophenone, p-Tolyl alcohol, Furfuryl thiopropionate, 2-Mercaptomethylpyrazine, 2,4-Heptadienal, cis-iso-Eugenol, S-Ethyl benzothioate, trans-Isoeugenol, Methyl 2-nitrobenzoate, Methyl o-methoxybenzoate, Guaiacyl acetate, 3-Methylthiophene, cis-4-Hepten-1-ol, beta-Phenoxy ethyl acetate, cis-3-Hexenyl lactate, meta-tolyl aldehyde, 4-(2-Furyl)-3-buten-2-one, Dimethyl disulfide, Cyclopentyl isobutyrate, Phenylacetaldehyde diethyl acetal, tetrahydrofurfuryl propionate, 2,5-Dimethylthiophene, Ethyl 2-methoxybenzyl ether, p-Methoxy-alpha-methyl cinnamaldehyde, Geranyl oxyacetaldehyde, Ethyl (p-tolyloxy)acetate, Trans-2-Hexenal, cis-4-Heptenal, 3-Mercapto-2-pentanone, 3,5,6-Trimethyl-3-cyclohexene-1-carbaldehyde, Floralol, 2,4-Dimethyl-3-cyclohexene-1-methanol, trans-2-Hexenal diethyl acetal, 3,6-ivy carbaldehyde, p-Methyl phenoxy acetaldehyde, (Z)-3-hexen-1-al, Dimethyl cyclohexene carboxaldehyde, 2,4-Dimethyl-3-Cyclohexene-1-carboxaldehyde, cis-3-Hexenyl pyruvate, 3,5-ivy carbaldehyde, delta-Octalactone, Methyl benzyl disulfide, 1-Phenylbutan-2-ol, Ethyl 2-methylbutyrate, Methyl mercaptan, Allyl anthranilate, Allyl tiglate, Ethanethiol, dimethyl sulfide 2-Propanethiol, (−)-Citronellol, Anisyl propionate, tert-Butyl mercaptan, 2,4-Pentadienal, 3,6-Nonadien-1-ol, Benzaldehyde diethyl acetal, 2-Thienyl mercaptan, 4-(p-Tolyl)-2-butanone, Isoeugenyl formate, 2,6-Nonadien-1-ol, 2-Methoxy-4-vinylphenol, p-Menth-8-en-3-ol, filbert heptenone, Gardamide, Dimethyl anthranilate, Allyl mercaptan, Ethyl anthranilate, cinnamon acrolein, Vanillin acetate, Isopulegol, Salicylaldehyde, Guaiacol, Hydratropaldehyde dimethyl acetal, Coumarin (Z)-2-hexen- 1-ol, (E)-2-hexen-1-ol, cis-3-Hexen-1-ol, Methyl isoeugenol, Isoeugenyl acetate, 2-phenyl propionaldehyde, 1-Phenyl-1-propanol, Methyl benzoate, Ethyl benzoate, Citronitrile, Styrallyl acetate, Butanoic acid, 2-methyl-, 2-hexenyl ester, (E)-, Vanitrope, 2-Methylindole, Eugenol, and combinations thereof.

12. The absorbent article of claim 11, wherein the 40% or more of the perfume raw materials also have an Odor Detection Threshold of about 7 or more −log molar concentration.

13. The absorbent article of claim 11, wherein about 40% to about 100%, by weight of the perfume, of the perfume raw materials have: a cyclodextrin binding coefficient of less than about 3.0, a ClogP of about 2.5 or less, and a weight average molecular weight of about 200 Daltons or less.

* * * * *